US009333235B2

(12) United States Patent
Madden et al.

(10) Patent No.: US 9,333,235 B2
(45) Date of Patent: *May 10, 2016

(54) COMBINATION THERAPY AND KIT FOR THE PREVENTION AND TREATMENT OF CYSTIC FIBROSIS

(71) Applicant: Trustees of Dartmouth College, Hanover, NH (US)

(72) Inventors: Dean R. Madden, Hanover, NH (US); Patrick R. Cushing, Woburn, MA (US); Prisca Boisguérin, Berlin (DE); Rudolf Volkmer, Nordwestuckermark (DE); Lars Vouilleme, Berlin (DE)

(73) Assignee: Trustees of Dartmouth College, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/105,646

(22) Filed: Dec. 13, 2013

(65) Prior Publication Data

US 2014/0100155 A1 Apr. 10, 2014

Related U.S. Application Data

(63) Continuation-in-part of application No. 13/292,151, filed on Nov. 9, 2011, now Pat. No. 8,999,919, which is a continuation-in-part of application No. 13/124,470, filed as application No. PCT/US2009/061246 on Oct. 20, 2009, now Pat. No. 8,415,292.

(60) Provisional application No. 61/107,438, filed on Oct. 22, 2008.

(51) Int. Cl.
| | |
|---|---|
| *A61K 38/16* | (2006.01) |
| *A61K 38/08* | (2006.01) |
| *A61K 45/06* | (2006.01) |
| *A61K 38/04* | (2006.01) |
| *A61K 38/10* | (2006.01) |
| *C07K 14/47* | (2006.01) |
| *C07K 5/103* | (2006.01) |
| *C07K 7/06* | (2006.01) |
| *C07K 7/08* | (2006.01) |
| *A61K 31/443* | (2006.01) |
| *A61K 31/47* | (2006.01) |

(52) U.S. Cl.
CPC .............. *A61K 38/16* (2013.01); *A61K 31/443* (2013.01); *A61K 31/47* (2013.01); *A61K 38/04* (2013.01); *A61K 38/08* (2013.01); *A61K 38/10* (2013.01); *A61K 45/06* (2013.01); *C07K 5/1013* (2013.01); *C07K 7/06* (2013.01); *C07K 7/08* (2013.01); *C07K 14/4703* (2013.01)

(58) Field of Classification Search
None
See application file for complete search history.

(56) References Cited

U.S. PATENT DOCUMENTS

| | | | | |
|---|---|---|---|---|
| 8,278,278 | B2 * | 10/2012 | Malkas et al. | 514/19.3 |
| 2005/0196754 | A1 | 9/2005 | Drmanac et al. | 435/6.11 |
| 2005/0214791 | A1 | 9/2005 | Sheppard et al. | 435/6.14 |
| 2005/0282743 | A1 | 12/2005 | Lu et al. | 514/1.2 |
| 2007/0044171 | A1 | 2/2007 | Kovalic et al. | 800/278 |
| 2007/0061916 | A1 | 3/2007 | Kovalic et al. | 800/278 |
| 2008/0069838 | A1 | 3/2008 | Peiris et al. | 424/221.1 |
| 2011/0201544 | A1 | 8/2011 | Madden et al. | 514/1.8 |

FOREIGN PATENT DOCUMENTS

WO WO 03/004604 A2 1/2003

OTHER PUBLICATIONS

Wolde et al., The Journal of Biological Chemistry (2007) 282(11), 8099-8109.*
Amacher et al. "Crystallization and Preliminary Diffraction Analysis of the CAL PDZ Domain in Complex with a Selective Peptide Inhibitor" Acta Crystallographica 2011 F67:600-603.
Bossard et al. "NHE-RF1 Protein Rescues ΔF508-CFTR Function" American Journal of Physiology—Lung Cellular and Molecular Physiology 2007 292: L1085-L1094.
Chen et al. "Computational Structure-based Redesign of Enzyme Activity" Proceedings of the National Academy of Sciences USA 2009 106(10):3764-3769.
Cheng et al. "A Golgi-associated PDZ Domain Protein Modulates Cystic Fibrosis Transmembrane Regulator Plasma Membrane Expression" The Journal of Biological Chemistry 2002 277(5):3520-3529.
Cushing et al. "The Relative Binding Affinities of PDZ Partners for CFTR: a Biochemical Basis for Efficient Endocytic Recycling" Biochemistry 2008 47:10084-10098.
Dasenbrook et al. "Persistent Methicillin-Resistant *Staphylococcus aureus* and Rate of $FEV_1$ Decline in Cystic Fibrosis" American Journal of Respiratory and Critical Care Medicine 2008 178:814-821.
Flume et al. "Ivacaftor in Subjects with Cystic Fibrosis Who Are Homozygous for the *F508del-CFTR* Mutation" Chest 2012 142(3):718-724.
Frey et al. "Predicting Resistant Mutations Using Protein Design Algorithms" Proceedings of the National Academy of Sciences USA 2010 107(31):13707-13712.
Georgiev et al. "The Minimized Dead-end Elimination Criterion and its Application to Protein Redesign in a Hybrid Scoring and Search Algorithm for Computing Partition Functions over Molecular Ensembles" Journal of Computational Chemistry 2008 29(10):1527-1542.
Guerra et al. "$Na^+/H^+$Exchanger Regulatory Factor Isoform 1 Overexpression Modulates Cystic Fibrosis Transmembrane Conductance Regulator (CFTR) Expression and Activity in Human Airway 16HBE14o—Cells and Rescues ΔF508 CFTR Functional Expression in Cystic Fibrosis Cells" The Journal of Biological Chemistry 2005 280(49):40925-40933.

(Continued)

*Primary Examiner* — Marcela M Cordero Garcia
*Assistant Examiner* — Catherine Mader
(74) *Attorney, Agent, or Firm* — Licata & Tyrrell P.C.

(57) ABSTRACT

A combination therapy and kit including an agent that inhibit the interaction between CAL and mutant CFTR proteins, in combination with a CFTR corrector, CFTR potentiator, mucolytic, anti-inflammatory agent or a combination thereof are provided as is a method for preventing or treating cystic fibrosis.

11 Claims, No Drawings

(56) References Cited

OTHER PUBLICATIONS

Guggino, W.B. and Stanton, B.A. "New Insights into Cystic Fibrosis: Molecular Switches that Regulate CFTR" Nature Reviews Molecular Cell Biology 2006 7(6):426-436.

Leach, A. R. and Lemon, A. P. "Exploring the Conformational Space of Protein Side Chains Using Dead-end Elimination and the A* Algorithm" Proteins: Structure, Function, and Genetics 1998 33:227-239.

Li, C. and Naren, A.P. "Macromolecular Complexes of Cystic Fibrosis Transmembrane Conductance Regulator and its Interacting Partners" Pharmacology & Therapeutics 2005 108(2):208-223.

Pedemonte et al. "Small-Molecule Correctors of Defective ΔF508-CFTR Cellular Processing Identified by High-Throughput Screening" The Journal of Clinical Investigation 2005 115(9):2564-2571.

Piserchio et al. "Association of the Cystic Fibrosis Transmembrane Regulator with CAL: Structural Features and Molecular Dynamics" Biochemistry 2005 44:16158-16166.

Que et al. "Improving Rate of Decline of $FEV_1$ in Young Adults with Cystic Fibrosis" Thorax 2006 61:155-157.

Ramsey et al. "A CFTR Potentiator in Patients with Cystic Fibrosis and the G551D Mutation" The New England Journal of Medicine 2011 365(18):1663-1672.

Reynolds et al. "Computational Redesign of the SHV-1 β-Lactamase/β-Lactamase Inhibitor Protein Interface" Journal of Molecular Biology 2008 382:1265-1275.

Schulz et al. "Immunocytochemical Detection of Somatostatin Receptors sstl, sst2A, sst2B, and sst3 in Paraffin-Embedded Breast Cancer Tissue Using Subtype-Specific Antibodies" Clinical Cancer Research 1998 6 (9):2047-2052.

Taylor-Robinson et al. "Understanding the Natural Progression in $\%FEV_1$ Decline in Patients with Cystic Fibrosis: A Longitudinal Study" Thorax 2012 67:860-866.

Van Goor et al. "Correction of the F508del-CFTR Protein Processing Defect In Vitro by the Investigational Drug VX-809" Proceedings of the National Academy of Sciences 2011 108(46):18843-18848.

Van Goor et al. "VX-809, A CFTR Corrector, Increases the Cell Surface Density of Functional F508del-CFTR in Pre-Clinical Models of Cystic Fibrosis" The $23^{rd}$ Annual North American Cystic Fibrosis Conference 2009 S9.4:154-155.

Wolde et al. "Targeting CAL as Negative Regulator of ΔF508-CFTR Cell-Surface Expression" The Journal of Biological Chemistry 2007 282(11):8099-8109.

Yamada et al. "Conformation of the Transmembrane Domains in Peripheral Myelin Protein 22. Part 1. Solution-Phase Synthesis and Circular Dichroism Study of Protected 17-Residue Partial Peptides in the First Putative Transmembrane Domain" The Journal of Peptide Research 2003 62:78-87.

Office Communication dated Jul. 23, 2012 from U.S. Appl. No. 13/124,470, filed Apr. 15, 2011.

Office Communication dated Aug. 28, 2013 from U.S. Appl. No. 13/292,151, filed Nov. 9, 2011.

International Search Report from PCT/US2009/061246, Aug. 25, 2010, PCT.

International Preliminary Report on Patentability from PCT/US2009/061246, May 5, 2011, PCT.

International Search Report From PCT/US2012/063486, Mar. 15, 2013, PCT.

International Preliminary Report on Patentability from PCT/US2012/063486, May 22, 2014, PCT.

* cited by examiner

SEQUENCE LISTING

```
<160> NUMBER OF SEQ ID NOS: 49

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes Met, Phe, Leu, Ala or Trp
<220> FEATURE:
<221> NAME/KEY: MISC_FEATURE
<222> LOCATION: (2)..(2)
<223> OTHER INFORMATION: Xaa denotes Gln, Pro, or Phe
<220> FEATURE:
<221> NAME/KEY: MISC_FEATURE
<222> LOCATION: (3)..(3)
<223> OTHER INFORMATION: Xaa independently denotes Ser, Val or Thr
<220> FEATURE:
<221> NAME/KEY: MISC_FEATURE
```

```
<222> LOCATION: (4)..(4)
<223> OTHER INFORMATION: Xaa independently denotes Ser or Thr
<220> FEATURE:
<221> NAME/KEY: MISC_FEATURE
<222> LOCATION: (5)..(5)
<223> OTHER INFORMATION: Xaa denotes Lys or Ile
<220> FEATURE:
<221> NAME/KEY: MISC_FEATURE
<222> LOCATION: (5)..(5)
<223> OTHER INFORMATION: Xaa denotes Lys Arg or Ile
<220> FEATURE:
<221> NAME/KEY: MISC_FEATURE
<222> LOCATION: (6)..(6)
<223> OTHER INFORMATION: Xaa denotes  Ile or Val.

<400> SEQUENCE: 1

Xaa Xaa Xaa Xaa Xaa Xaa
1               5

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Cys Ala Asn Gly Leu Met Gln Thr Ser Lys Ile
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Cys Gly Leu Met Gln Thr Ser Lys Ile
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Cys Phe Phe Ser Thr Ile Ile
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Cys Phe Phe Thr Ser Ile Ile
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide
```

<400> SEQUENCE: 6

Cys Met Gln Thr Ser Ile Ile
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Cys Met Gln Thr Ser Lys Ile
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Cys Trp Gln Thr Ser Ile Ile
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Cys Trp Pro Thr Ser Ile Ile
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Cys Thr Trp Gln Thr Ser Ile Ile
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Cys Lys Trp Gln Thr Ser Ile Ile
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Pro His Trp Gln Thr Ser Ile Ile
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Phe His Trp Gln Thr Ser Ile Ile
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

Ser Arg Trp Gln Thr Ser Ile Ile
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide

<400> SEQUENCE: 15

Cys Ala Asn Ser Arg Trp Gln Thr Ser Ile Ile
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

Gly Leu Trp Pro Thr Ser Ile Ile
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

Ser Arg Trp Pro Thr Ser Ile Ile
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

```
Phe Pro Trp Pro Thr Ser Ile Ile
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Modified with fluorescein

<400> SEQUENCE: 19

Ala Asn Ser Arg Trp Pro Thr Ser Ile Ile
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Ala Asn Ser Arg Trp Pro Thr Ser Ile Ile
1               5                   10

<210> SEQ ID NO 21
<211> LENGTH: 10
<212> TYPE: PRT
<213> ORGANISM: Artificial sequence
<220> FEATURE:
<223> OTHER INFORMATION: Synthetic peptide

<400> SEQUENCE: 21

Ala Asn Ser Arg Leu Pro Thr Ser Ile Ile
1               5                   10

<210> SEQ ID NO 22
<211> LENGTH: 10
<212> TYPE: PRT
<213> ORGANISM: Artificial sequence
<220> FEATURE:
<223> OTHER INFORMATION: Synthetic peptide

<400> SEQUENCE: 22

Ala Asn Ser Arg Ala Pro Thr Ser Ile Ile
1               5                   10

<210> SEQ ID NO 23
<211> LENGTH: 6
<212> TYPE: PRT
<213> ORGANISM: Artificial sequence
<220> FEATURE:
<223> OTHER INFORMATION: Synthetic peptide

<400> SEQUENCE: 23

Trp Gln Val Thr Arg Val
1               5

<210> SEQ ID NO 24
<211> LENGTH: 6
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes Met, Phe, Leu, or Ala.
<220> FEATURE:
<221> NAME/KEY: MISC_FEATURE
<222> LOCATION: (2)..(2)
<223> OTHER INFORMATION: Xaa denotes Gln, Pro, or Phe.
<220> FEATURE:
<221> NAME/KEY: MISC_FEATURE
<222> LOCATION: (3)..(3)
<223> OTHER INFORMATION: Xaa denotes Ser, Val or Thr.
<220> FEATURE:
<221> NAME/KEY: MISC_FEATURE
<222> LOCATION: (4)..(4)
<223> OTHER INFORMATION: Xaa denotes Ser or Thr.
<220> FEATURE:
<221> NAME/KEY: MISC_FEATURE
<222> LOCATION: (5)..(5)
<223> OTHER INFORMATION: Xaa denotes Lys, Arg or Ile.
<220> FEATURE:
<221> NAME/KEY: MISC_FEATURE
<222> LOCATION: (6)..(6)
<223> OTHER INFORMATION: Xaa denotes Ile or Val.

<400> SEQUENCE: 24

Xaa Xaa Xaa Xaa Xaa Xaa
1               5

<210> SEQ ID NO 25
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue.
<220> FEATURE:
<221> NAME/KEY: MISC_FEATURE
<222> LOCATION: (5)..(5)
<223> OTHER INFORMATION: Modified with fluorescein.

<400> SEQUENCE: 25

Trp Arg Phe Lys Lys Ala Asn Ser Arg Trp Pro Thr Ser Ile Ile
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue.

<400> SEQUENCE: 26

Trp Arg Phe Lys Lys Ala Asn Ser Arg Trp Pro Thr Ser Ile Ile
1               5                   10                  15

<210> SEQ ID NO 27
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
```

```
<223> OTHER INFORMATION: D-amino acid residue.
<220> FEATURE:
<221> NAME/KEY: MISC_FEATURE
<222> LOCATION: (5)..(5)
<223> OTHER INFORMATION: Modified with 6-carboxy-X-rhodamine.

<400> SEQUENCE: 27

Trp Arg Phe Lys Lys Ala Asn Ser Arg Trp Pro Thr Ser Ile Ile
1               5                   10                  15

<210> SEQ ID NO 28
<211> LENGTH: 10
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(4)
<223> OTHER INFORMATION: D-amino acid residue.

<400> SEQUENCE: 28

Pro Asn Glu Ala Trp Pro Thr Ser Ile Ile
1               5                   10

<210> SEQ ID NO 29
<211> LENGTH: 10
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(1)
<223> OTHER INFORMATION: D-amino acid residue.
<220> FEATURE:
<221> NAME/KEY: MISC_FEATURE
<222> LOCATION: (3)..(3)
<223> OTHER INFORMATION: D-amino acid residue.

<400> SEQUENCE: 29

Phe Asn Ala Arg Trp Gln Thr Ser Ile Ile
1               5                   10

<210> SEQ ID NO 30
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-amino acid residue.

<400> SEQUENCE: 30

Phe Asn Ser Arg Trp Gln Thr Ser Ile Ile
1               5                   10

<210> SEQ ID NO 31
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid residue.

<400> SEQUENCE: 31
```

```
Lys Asn Ser Arg Trp Gln Thr Ser Ile Ile
1               5                   10
```

<210> SEQ ID NO 32
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: D-amino acid residue.

<400> SEQUENCE: 32

```
Pro Asn Ser Arg Trp Gln Thr Ser Ile Ile
1               5                   10
```

<210> SEQ ID NO 33
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue.

<400> SEQUENCE: 33

```
Ala Asn Ser Arg Trp Gln Thr Ser Ile Ile
1               5                   10
```

<210> SEQ ID NO 34
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-amino acid residue.

<400> SEQUENCE: 34

```
Trp Arg Phe Lys Lys
1               5
```

<210> SEQ ID NO 35
<211> LENGTH: 7
<212> TYPE: PRT
<213> ORGANISM: Artificial sequence
<220> FEATURE:
<223> OTHER INFORMATION: Synthetic peptide

<400> SEQUENCE: 35

```
Leu Glu Val Leu Phe Gln Gly
1               5
```

<210> SEQ ID NO 36
<211> LENGTH: 6
<212> TYPE: PRT
<213> ORGANISM: Artificial sequence
<220> FEATURE:
<223> OTHER INFORMATION: Synthetic peptide

<400> SEQUENCE: 36

```
Trp Gln Thr Ser Ile Ile
```

<210> SEQ ID NO 37
<211> LENGTH: 4
<212> TYPE: PRT
<213> ORGANISM: Artificial sequence
<220> FEATURE:
<223> OTHER INFORMATION: Synthetic peptide

<400> SEQUENCE: 37

Thr Ser Ile Ile
1

<210> SEQ ID NO 38
<211> LENGTH: 10
<212> TYPE: PRT
<213> ORGANISM: Artificial sequence
<220> FEATURE:
<223> OTHER INFORMATION: Synthetic peptide

<400> SEQUENCE: 38

Ala Asn Gly Leu Met Gln Thr Ser Lys Leu
1               5                   10

<210> SEQ ID NO 39
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa denotes any amino acid residue.
<220> FEATURE:
<221> NAME/KEY: MISC_FEATURE
<222> LOCATION: (2)..(2)
<223> OTHER INFORMATION: Xaa denotes Ser or Thr.
<220> FEATURE:
<221> NAME/KEY: MISC_FEATURE
<222> LOCATION: (3)..(3)
<223> OTHER INFORMATION: Xaa denotes any amino acid residue.
<220> FEATURE:
<221> NAME/KEY: MISC_FEATURE
<222> LOCATION: (4)..(4)
<223> OTHER INFORMATION: Xaa denotes Leu, Val or Ile.

<400> SEQUENCE: 39

Xaa Xaa Xaa Xaa
1

<210> SEQ ID NO 40
<211> LENGTH: 10
<212> TYPE: PRT
<213> ORGANISM: Artificial sequence
<220> FEATURE:
<223> OTHER INFORMATION: Synthetice peptide

<400> SEQUENCE: 40

Thr Glu Glu Glu Val Gln Asp Thr Arg Leu
1               5                   10

<210> SEQ ID NO 41
<211> LENGTH: 6
<212> TYPE: PRT
<213> ORGANISM: Artificial sequence
<220> FEATURE:
<223> OTHER INFORMATION: Synthetic peptide

<400> SEQUENCE: 41

```
Trp Gln Asp Ser Gly Ile
1               5
```

<210> SEQ ID NO 42
<211> LENGTH: 27
<212> TYPE: PRT
<213> ORGANISM: Artificial sequence
<220> FEATURE:
<223> OTHER INFORMATION: Synthetic peptide

<400> SEQUENCE: 42

```
Gly Ala Leu Phe Leu Gly Phe Leu Gly Ala Ala Gly Ser Thr Met Gly
1               5                   10                  15

Ala Trp Ser Gln Pro Lys Lys Arg Lys Val
            20                  25
```

<210> SEQ ID NO 43
<211> LENGTH: 8
<212> TYPE: PRT
<213> ORGANISM: Artificial sequence
<220> FEATURE:
<223> OTHER INFORMATION: Synthetic peptide

<400> SEQUENCE: 43

```
Arg Arg Arg Arg Arg Arg Arg Arg
1               5
```

<210> SEQ ID NO 44
<211> LENGTH: 14
<212> TYPE: PRT
<213> ORGANISM: Artificial sequence
<220> FEATURE:
<223> OTHER INFORMATION: Synthetic peptide

<400> SEQUENCE: 44

```
Gly Arg Lys Lys Arg Arg Gln Arg Arg Arg Pro Pro Gln Gln
1               5                   10
```

<210> SEQ ID NO 45
<211> LENGTH: 27
<212> TYPE: PRT
<213> ORGANISM: Artificial sequence
<220> FEATURE:
<223> OTHER INFORMATION: Synthetic peptide

<400> SEQUENCE: 45

```
Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

<210> SEQ ID NO 46
<211> LENGTH: 21
<212> TYPE: PRT
<213> ORGANISM: Artificial sequence
<220> FEATURE:
<223> OTHER INFORMATION: Synthetic peptide

<400> SEQUENCE: 46

```
Ala Gly Tyr Leu Leu Gly Lys Ile Asn Leu Lys Ala Leu Ala Ala Leu
1               5                   10                  15

Ala Lys Lys Ile Leu
            20
```

```
<210> SEQ ID NO 47
<211> LENGTH: 18
<212> TYPE: PRT
<213> ORGANISM: Artificial sequence
<220> FEATURE:
<223> OTHER INFORMATION: Synthetic peptide

<400> SEQUENCE: 47

Lys Leu Ala Leu Lys Leu Ala Leu Lys Ala Leu Lys Ala Ala Leu Lys
1               5                   10                  15

Leu Ala

<210> SEQ ID NO 48
<211> LENGTH: 27
<212> TYPE: PRT
<213> ORGANISM: Artificial sequence
<220> FEATURE:
<223> OTHER INFORMATION: Synthetic peptide

<400> SEQUENCE: 48

Gly Ala Leu Phe Leu Ala Phe Leu Ala Ala Leu Ser Leu Met Gly
1               5                   10                  15

Leu Trp Ser Gln Pro Lys Lys Lys Arg Lys Val
                20                  25

<210> SEQ ID NO 49
<211> LENGTH: 16
<212> TYPE: PRT
<213> ORGANISM: Artificial sequence
<220> FEATURE:
<223> OTHER INFORMATION: Synthetic peptide

<400> SEQUENCE: 49

Arg Gln Ile Lys Ile Trp Phe Gln Asn Arg Arg Met Lys Trp Lys Lys
1               5                   10                  15
```

COMBINATION THERAPY AND KIT FOR THE PREVENTION AND TREATMENT OF CYSTIC FIBROSIS

INTRODUCTION

This application is a continuation-in-part application of U.S. patent application Ser. No. 13/292,151, filed Nov. 9, 2011, which is a continuation-in-part application of U.S. patent application Ser. No. 13/124,470, filed Apr. 15, 2011, now U.S. Pat. No. 8,415,292, which claims the benefit of priority of PCT/US2009/061246, filed Oct. 20, 2009, and U.S. Provisional Application No. 61/107,438, filed Oct. 22, 2008, which are incorporated herein by reference in their entireties.

This invention was made with government support under grant numbers R01-DK075309, P20-RR018787 and R01 GM-78031 awarded by the National Institutes of Health. The government has certain rights in the invention. Work on this invention was also supported by grants from the Cystic Fibrosis Foundation.

BACKGROUND

CFTR (Cystic Fibrosis Transmembrane Conductance Regulator) is the target of mutations that cause cystic fibrosis (CF). CF is characterized by abnormal endocrine and exocrine gland function. In CF, unusually thick mucus leads to chronic pulmonary disease and respiratory infections, insufficient pancreatic and digestive function, and abnormally concentrated sweat. Seventy percent of the mutant CFTR alleles in the Caucasian population result from deletion of phenylalanine at position 508 ($\Delta$F508-CFTR), the result of a three base pair deletion in the genetic code. Other mutations have also been described, e.g., a glycine to aspartate substitution at position 551 (G551D-CFTR) occurs in approximately 3-4% of cystic fibrosis patients.

The $\Delta$F508-CFTR mutation results in a CFTR protein capable of conducting chloride, but absent from the plasma membrane because of aberrant intracellular processing. Under usual conditions (37° C.), the $\Delta$F508-CFTR protein is retained in the endoplasmic reticulum (ER), by prolonged association with the ER chaperones, including calnexin and hsp70. Over expression of $\Delta$F508-CFTR can result in $\Delta$F508-CFTR protein appearing at the cell surface, and this protein is functional once it reaches the cell surface. The $\Delta$F508-CFTR "trafficking" block is also reversible by incubation of cultured CF epithelial cells at reduced temperatures (25-27° C.). Lowered temperature results in the appearance of CFTR protein and channel activity at the cell surface, suggesting an intrinsic thermodynamic instability in $\Delta$F508-CFTR at 37° C. that leads to recognition of the mutant protein by the ER quality control mechanism, prevents further trafficking, and results in protein degradation. Chemical chaperones are currently being developed to restore the folding of $\Delta$F508-CFTR. However, when $\Delta$F508-CFTR is expressed at the cell-surface following treatment, CAL (also known as CFTR-associated ligand, PIST, GOPC, ROS, and FIG) directs the lysosomal degradation of CFTR in a dose-dependent fashion and reduces the amount of CFTR found at the cell surface. Conversely, NHERF1 and NHERF2 functionally stabilize CFTR. Consistent with this role of CAL, RNA interference targeting of endogenous CAL also increases cell-surface expression of the disease-associated $\Delta$F508-CFTR mutant and enhances transepithelial chloride currents in a polarized human patient bronchial epithelial cell line (Wolde, et al. (2007) *J. Biol. Chem.* 282:8099-8109).

Current treatments for cystic fibrosis generally focus on controlling infection through antibiotic therapy and promoting mucus clearance by use of postural drainage and chest percussion. However, even with such treatments, frequent hospitalization is often required as the disease progresses. New therapies designed to increase chloride ion conductance in airway epithelial cells have been proposed, and restoration of the expression of functional CFTR at the cell surface is considered a major therapeutic goal in the treatment of cystic fibrosis, a disease that affects ~30,000 patients in the U.S., and ~70,000 patients worldwide. For example, KALYDECO (Ivacaftor; VX-770) is an FDA-approved compound that 'potentiates' the open probability ($P_o$) of CFTR channels, including the G551D mutant, and thus ameliorates the underlying molecular lesion in this group of patients. A 48-week clinical trial showed excellent efficacy, including a 10.6% improvement in lung function (predicted forced expiratory volume in 1 second; FEV1), a 55% drop in pulmonary exacerbations, and a 48 mEq/L reduction in sweat chloride (Ramsey, et al. (2011) *N. Engl. J. Med.* 365:1663-72). While showing efficacy in subjects with the G551D mutation, KALYDECO is not useful as a monotherapy for the largest group of CF patients. In ~70% of mutant alleles, Phe508 is deleted ($\Delta$F508; Kerem, et al. (1989) *Science* 245: 1073-1080). As a result, ~50% of CF patients are $\Delta$F508 homozygous and ~40% are heterozygous. Unfortunately, clinical trials in $\Delta$F508 homozygotes show low efficacy for KALYDECO alone (Flume, et al. (2012) *Chest* 142:718-724).

In the absence of interventions, $\Delta$F508-CFTR exhibits three defects: folding, gating, and stability (Riordan (2008) *Annu. Rev. Biochem.* 77:701-726; Cheng, et al. (1990) *Cell* 63:827-834; Lukacs, et al. (1993) *J. Biol. Chem.* 268:21592-21598; Dalemans, et al. (1991) *Nature* 354:526-528). However, if folding is restored, $\Delta$F508-CFTR retains some channel activity (Drumm, et al. (1991) *Science* 254:1797-1799; Denning, et al. (1992) *Nature* 358:761-764). 'Corrector' compounds have been identified such as corr-4a (Pedemonte et al. (2005) *J. Clin. Invest.* 115:2564) and Lumacaftor (VX-809), which partially alleviate the folding defect and allows some $\Delta$F508-CFTR to reach the apical membrane (Van Goor, et al. (2009) *Pediatr. Pulmonol.* 44:S154-S155; Van Goor, et al. (2011) *Proc. Natl. Acad. Sci. USA* 108:18843-18848). Although Lumacaftor yields only limited benefits in monotherapy, it shows greater efficacy in combination with KALYDECO: 25% of patients showed a >10% increase in FEV1 and 55% of patients showed >5% increase, with few adverse effects. While a 5% or 10% improvement is clinically meaningful, $FEV_1$ drops approximately 1-2% per year in CF patients (Dasenbrook, et al. (2008) *Am. J. Respir. Crit. Care Med.* 178:814-821; Que, et al. (2006) *Thorax* 61:155-157), even in the absence of acceleration by pulmonary exacerbations (Taylor-Robinson, et al. (2012) *Thorax* 67:860-866). Thus, further improvements are required, especially for non-responders and the 40% of $\Delta$F508-CFTR heterozygous patients.

SUMMARY OF THE INVENTION

The present invention is a method for preventing or treating cystic fibrosis by administering to a subject in need of treatment an effective amount of an agent that selectively inhibits the interaction between a degradation-prone CFTR and CAL in combination with a CFTR corrector, CFTR potentiator, mucolytic, anti-inflammatory agent or a combination thereof, thereby preventing or treating the subject's cystic fibrosis. In one embodiment, the degradation-prone CFTR is $\Delta$F508

CFTR or R1066C CFTR. In other embodiments, the agent is a peptide or peptidomimetic (e.g., 6 to 20 residues in length). In certain embodiments, the peptide has the amino acid sequence of SEQ ID NO:1, or a derivative thereof, or is a peptide as listed in Table 1. Moreover, in other embodiments, the peptide is derivatized with a label, one or more post-translational modifications, a cell-penetrating sequence (e.g., having an amino acid sequence of SEQ ID NO:42), or a combination thereof. In still other embodiments, the peptidomimetic is a mimetic of the amino acid sequence of SEQ ID NO:1 or is a peptidomimetic as listed in Table 3. A kit containing an agent that inhibits the interaction between a degradation-prone CFTR and CAL; and a CFTR corrector, CFTR potentiator, mucolytic, anti-inflammatory agent or a combination thereof, is also provided.

DETAILED DESCRIPTION OF THE INVENTION

Novel inhibitors have now been identified that block the interaction or binding of CFTR with the CAL PDZ binding site by competitive displacement. By inhibiting this interaction with CAL, degradation-prone CFTR proteins are stabilized and the amount of CFTR protein at the cell surface is effectively increased. Indeed, representative peptide and peptidomimetic CAL inhibitors were shown to increase the apical cell-surface expression and transepithelial chloride efflux of the most common CFTR mutation associated with CF. Accordingly, inhibitors of the present invention find application in increasing the cell surface expression of degradation-prone CFTR proteins and in the treatment for CF. In particular, CAL inhibition is of use in combination therapies for reversing the ΔF508 stability defect.

As used herein, "cell surface expression" of a CFTR protein refers to CFTR protein which has been transported to the surface of a cell. In this regard, an agent that increases the cell surface expression of a CFTR protein refers to an agent that increases the amount of CFTR protein, which is present or detected at the plasma membrane of a cell, as compared to a cell which is not contacted with the agent.

Genetic, biochemical, and cell biological studies have revealed a complex network of protein-protein interactions that are required for correct CFTR trafficking, including a number of PDZ (PSD-95, discs-large, zonula occludens-1) proteins, which act as adaptor molecules, coupling CFTR to other components of the trafficking and localization machinery, and to other transmembrane channels and receptors (Kunzelmann (2001) *News Physiol. Sci.* 16:167-170; Guggino & Stanton (2006) *Nat. Rev. Mol. Cell Biol.* 7:426-436). Class I PDZ domains typically recognize C-terminal binding motifs characterized by the sequence -(Ser/Thr)-X-Φ-COOH (where Φ represents a hydrophobic side chain, and X represents any amino acid) (Harris & Lim (2001) *J. Cell Sci.* 114:3219-3231; Brône & Eggermont (2005) *Am. J. Physiol.* 288:C20-C29). The cytoplasmic C-terminus of CFTR satisfies the class I PDZ binding motif, ending in the sequence -Thr-Arg-Leu (Hall, et al. (1998) *Proc. Natl. Acad. Sci. USA* 95:8496-8501; Short, et al. (1998) *J. Biol. Chem.* 273: 19797-19801; Wang, et al. (1998) *FEBS Lett.* 427:103-108) and it has been demonstrated that CFTR C-terminal PDZ-binding motif controls retention of the protein at the apical membrane and modulates its endocytic recycling (Moyer, et al. (2000) *J. Biol. Chem.* 275:27069-27074; Swiatecka-Urban, et al. (2002) *J. Biol. Chem.* 277:40099-40105). PDZ proteins that have been shown to bind or interact with CFTR include NHERF1 (Na+/H+ exchanger regulatory factor 1; also known as EBP50), NHERF2 (Na+/H+ exchanger regulatory factor 2, also known as E3KARP), NHERF3 (Na+/H+ exchanger regulatory factor 3, also known as CAP70, PDZK1, or NaPi CAP-1), NHERF4 (Na+/H+ exchanger regulatory factor 4, also known as IKEPP or NaPi CAP-2), and CAL (CFTR-associated ligand; also known as PIST, GOPC, and FIG; GENBANK Accession Nos. NP_065132 and NP_001017408, incorporated herein by reference) (Guggino & Stanton (2006) supra; Li & Naren (2005) *Pharmacol. Ther.* 108:208-223). Of these proteins, CAL has been shown to reduce the levels of recombinant wild-type CFTR found in whole cell lysates and at the cell surface, whereas overexpression of NHERF1 together with CAL can block this effect on both wild-type and ΔF508-CFTR (Cheng, et al. (2002) *J. Biol. Chem.* 277:3520-3529; Guerra, et al. (2005) *J. Biol. Chem.* 280:40925-40933). Moreover, RNAi targeting of endogenous CAL specifically increases cell surface expression of the ΔF508-CFTR mutant protein and enhances transepithelial chloride currents in a polarized human patient bronchial epithelial cell line (Wolde, et al. (2007) *J. Biol. Chem.* 282:8099-8109). These data indicate that the PDZ proteins which interact with CFTR have opposing functions. Thus, targeting the interaction of CAL with CFTR can stabilize a mutant CFTR protein and facilitate cell surface expression of the same.

The CFTR protein and mutants thereof are well-known in the art and wild-type human CFTR is disclosed in GENBANK Accession No. NP_000483, incorporated herein by reference. Misfolding of mutant CFTR proteins has been shown to dramatically augment the ubiquitination susceptibility of the protein in post-Golgi compartments (Swiatecka-Urban, et al. (2005) *J. Biol. Chem.* 280:36762). Thus, for the purposes of the present invention, the term "degradation-prone" when used as a modifier of a CFTR protein, refers to a mutant CFTR protein that exhibits an increased rate of degradation following initial trafficking to the cell surface and a decrease in the amount of CFTR protein present at the cell surface (i.e., plasma membrane). Examples of degradation-prone CFTR proteins include, but are not limited to ΔF508 CFTR and Δ70F CFTR (see Sharma, et al. (2004) *J. Cell Biol.* 164:923). Other degradation-prone CFTR proteins are known in the art and/or can be identified by routine experimentation. For example, the rate or amount of transport of CFTR protein from the cell surface can be determined by detecting the amount of complex-glycosylated CFTR protein present at the cell surface, in endoplasmic vesicles and/or in lysosomes using methods such as cell surface immunoprecipitation or biotinylation or cell immunocytochemistry with an antibody specific for CFTR protein. Additional methods, both in vivo and in vitro, are known in the art that can be used for detecting an increase or decrease in cell surface expression of a CFTR protein.

Because PDZ proteins share overlapping specificities, particular embodiments of this invention embrace inhibitory agents that selectively block the interaction or binding between a degradation-prone CFTR and CAL. As used herein, a "selective inhibitor of the CFTR and CAL interaction" or "an agent that selectively inhibits the interaction between the degradation-prone CFTR and CAL" is any molecular species that is an inhibitor of the CFTR and CAL interaction but which fails to inhibit, or inhibits to a substantially lesser degree the interaction between CFTR and proteins that stabilize degradation-prone CFTR, e.g., NHERF1 AND NHERF2. Methods for assessing the selectively of an inhibitor of the CFTR and CAL interaction are disclosed herein and can be carried out in in vitro or in vivo assays.

By way of illustration, libraries of agents were screened for the ability to increase the amount of ΔF508 CFTR at the apical membrane and to increase the CFTR-mediated chloride efflux across monolayers of CFBE41O-cells. The magnitude of the functional rescue of the mutant CFTR protein correlated with the selectivity of the agent for CAL versus NHERF1 and NHERF2, namely, the more selective the agent for the CAL binding site, the more effective the agent was at enhancing chloride efflux. Moreover, upon further refinement, off-site targets were eliminated by modification of the amino acid residue at $P^{-5}$ (see Example 4).

Accordingly, the present invention features compositions and methods for facilitating the cell surface expression of mutant CFTR by selectively blocking the interaction between a degradation-prone CFTR and CAL. Agents of the present invention can be any molecular species, with particular embodiments embracing peptides or mimetics thereof.

As used herein, the term "peptide" denotes an amino acid polymer that is composed of at least two amino acids covalently linked by an amide bond. Peptides of the present invention are desirably 6 to 20 residues in length, or more desirably 7 to 15 residues in length. In certain embodiments, a selective inhibitor of the CFTR and CAL interaction is a 6 to 20 residue peptide containing the amino acid sequence $Xaa_1$-$Xaa_2$-$Xaa_3$-$Xaa_4$-$Xaa_5$-$Xaa_6$ (SEQ ID NO:1), wherein $Xaa_1$ is Met, Phe, Leu, Ala or Trp; $Xaa_2$ is Gln, Pro, or Phe; $Xaa_3$ is Ser, Val or Thr; $Xaa_4$ is Ser or Thr; $Xaa_5$ is Lys, Arg or Ile; and $Xaa_6$ is Ile or Val. In certain embodiments of the present invention, a selective inhibitor of the CFTR and CAL interaction is a peptide having an amino acid sequence as listed in Table 1.

TABLE 1

| Peptide Designation | Peptide Sequence | SEQ ID NO: |
|---|---|---|
| PRC 01 | CANGLMQTSKI | 2 |
| PRC 02 | CGLMQTSKI | 3 |
| PRC 03 | CFFSTII | 4 |
| PRC 04 | CFFTSII | 5 |
| PRC 05 | CMQTSII | 6 |
| PRC 06 | CMQTSKI | 7 |
| PRC 07 | CWQTSII | 8 |
| PRC 08 | CWPTSII | 9 |
| PRC 09 | CTWQTSII | 10 |
| PRC 10 | CKWQTSII | 11 |
| PRC 11 | PHWQTSII | 12 |
| PRC 12 | FHWQTSII | 13 |
| PRC 13 | SRWQTSII | 14 |
| PRC 17 | CANSRWQTSII | 15 |
| PRC 25 | GLWPTSII | 16 |
| PRC 26 | SRWPTSII | 17 |
| PRC 27 | FPWPTSII | 18 |
| PRC 30 or F*-iCal36 | *FITC-ANSRWPTSII | 19 |
| PRC 36 or iCal36 | ANSRWPTSII | 20 |
| iCAL42 | ANSRLPTSII | 21 |
|  | ANSRAPTSII | 22 |
| kCAL01 | WQVTRV | 23 |

FITC = fluorescein.

In particular embodiments of the present invention, a selective inhibitor of the CFTR and CAL interaction is a peptide that binds to CAL, but fails to bind to any other lung epithelial cell protein containing a PDZ domain including but not limited to TIP-1, NHERF1 and NHERF2. In accordance with this embodiment, the inhibitor is "CAL selective." CAL selective inhibitors are desirably 6 to 20 residue peptide and contain the amino acid sequence $Xaa_7$-$Xaa_8$-$Xaa_9$-$Xaa_{10}$-$Xaa_{11}$-$Xaa_{12}$ (SEQ ID NO:24), wherein $Xaa_7$ is Met, Phe, Leu, or Ala; $Xaa_8$ is Gln, Pro, or Phe; $Xaa_9$ is Ser, Val or Thr; $Xaa_{10}$ is Ser or Thr; $Xaa_{11}$ is Lys, Arg or Ile; and $Xaa_{12}$ is Ile or Val. In specific embodiments, a CAL selective inhibitor is a peptide of SEQ ID NO:20, SEQ ID NO:21 or SEQ ID NO:22.

In accordance with the present invention, derivatives of the peptides of the invention are also provided. As used herein, a peptide derivative is a molecule which retains the primary amino acids of the peptide, however, the N-terminus, C-terminus, and/or one or more of the side chains of the amino acids therein have been chemically altered or derivatized. Such derivatized peptides include, for example, naturally occurring amino acid derivatives, for example, 4-hydroxyproline for proline, 5-hydroxylysine for lysine, homoserine for serine, ornithine for lysine, and the like. Other derivatives or modifications include, e.g., a label, such as fluorescein or tetramethylrhodamine; or one or more post-translational modifications such as acetylation, amidation, formylation, hydroxylation, methylation, phosphorylation, sulfatation, glycosylation, or lipidation. Indeed, certain chemical modifications, in particular N-terminal glycosylation, have been shown to increase the stability of peptides in human serum (Powell et al. (1993) *Pharma. Res.* 10:1268-1273). Peptide derivatives also include those with increased membrane permeability obtained by N-myristoylation (Brand, et al. (1996) *Am. J. Physiol. Cell. Physiol.* 270:C1362-C1369). An exemplary peptide derivative is provided in SEQ ID NO:19 (Table 1).

In addition, a peptide derivative of the invention can include a cell-penetrating sequence which facilitates, enhances, or increases the transmembrane transport or intracellular delivery of the peptide into a cell. For example, a variety of proteins, including the HIV-1 Tat transcription factor, *Drosophila* Antennapedia transcription factor, as well as the herpes simplex virus VP22 protein have been shown to facilitate transport of proteins into the cell (Wadia and Dowdy (2002) *Curr. Opin. Biotechnol.* 13:52-56). Further, an arginine-rich peptide (Futaki (2002) *Int. J. Pharm.* 245:1-7), a polylysine peptide containing Tat PTD (Hashida, et al. (2004) *Br. J. Cancer* 90(6):1252-8), Pep-1 (Deshayes, et al. (2004) *Biochemistry* 43(6):1449-57) or an HSP70 protein or fragment thereof (WO 00/31113) is suitable for enhancing intracellular delivery of a peptide or peptidomimetic of the invention into the cell. Examples of known cell-penetrating peptides (CPP) are provided in Table 2.

TABLE 2

| CPP | Sequence | SEQ ID NO: |
|---|---|---|
| MPG | GALFLGFLGAAGSTMGAWSQPKKKRKV | 42 |
| R8 | RRRRRRRR | 43 |
| Tat (48-60) | GRKKRRQRRRPPQQ | 44 |
| Transportan | GWTLNSAGYLLGKINLKALAALAKKIL | 45 |
| TP10 | AGYLLGKINLKALAALAKKIL | 46 |

TABLE 2-continued

| CPP | Sequence | SEQ ID NO: |
|---|---|---|
| MAP | KLALKLALKALKAALKLA | 47 |
| MPG-a | GALFLAFLAAALSLMGLWSQPKKKRKV | 48 |
| Penetratin | RQIKIWFQNRRMKWKK | 49 |

Exemplary cell penetrating peptides include WrFKK (SEQ ID NO:34) and MPG (SEQ ID NO:42).

While a peptide of the invention can be derivatized with by one of the above indicated modifications, it is understood that a peptide of this invention may contain more than one of the above described modifications within the same peptide.

As indicated, the present invention also encompasses peptidomimetics of the peptides disclosed herein. Peptidomimetics refer to a synthetic chemical compound which has substantially the same structural and/or functional characteristics of the peptides of the invention. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy the activity of the mimetic. Routine testing can be used to determine whether a mimetic has the requisite activity, e.g., that it can inhibit the interaction between CFTR and CAL. The phrase "substantially the same," when used in reference to a mimetic or peptidomimetic, means that the mimetic or peptidomimetic has one or more activities or functions of the referenced molecule, e.g., selective inhibition of the CAL and CFTR interaction.

There are clear advantages for using a mimetic of a given peptide. For example, there are considerable cost savings and improved patient compliance associated with peptidomimetics, since they can be administered orally compared with parenteral administration for peptides. Furthermore, peptidomimetics are much cheaper to produce than peptides.

Thus, peptides described above have utility in the development of such small chemical compounds with similar biological activities and therefore with similar therapeutic utilities. The techniques of developing peptidomimetics are conventional. For example, peptide bonds can be replaced by non-peptide bonds or non-natural amino acids that allow the peptidomimetic to adopt a similar structure, and therefore biological activity, to the original peptide. Further modifications can also be made by replacing chemical groups of the amino acids with other chemical groups of similar structure. The development of peptidomimetics can be aided by determining the tertiary structure of the original peptide, either free or bound to a CAL protein, by NMR spectroscopy, crystallography and/or computer-aided molecular modeling. These techniques aid in the development of novel compositions of higher potency and/or greater bioavailability and/or greater stability than the original peptide (Dean (1994) *BioEssays* 16:683-687; Cohen & Shatzmiller (1993) *J. Mol. Graph.* 11:166-173; Wiley & Rich (1993) *Med. Res. Rev.* 13:327-384; Moore (1994) *Trends Pharmacol. Sci.* 15:124-129; Hruby (1993) *Biopolymers* 33:1073-1082; Bugg, et al. (1993) *Sci. Am.* 269:92-98). Once a potential peptidomimetic compound is identified, it may be synthesized and assayed using an assay described herein or any other appropriate assay for monitoring cell surface expression of CFTR.

It will be readily apparent to one skilled in the art that a peptidomimetic can be generated from any of the peptides described herein. It will furthermore be apparent that the peptidomimetics of this invention can be further used for the development of even more potent non-peptidic compounds, in addition to their utility as therapeutic compounds.

Peptide mimetic compositions can contain any combination of non-natural structural components, which are typically from three structural groups: residue linkage groups other than the natural amide bond ("peptide bond") linkages; non-natural residues in place of naturally occurring amino acid residues; residues which induce secondary structural mimicry, i.e., induce or stabilize a secondary structure, e.g., a beta turn, gamma turn, beta sheet, alpha helix conformation, and the like; or other changes which confer resistance to proteolysis. For example, a polypeptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropyl-carbodiimide (DIC). Linking groups alternative to the amide bond include, for example, ketomethylene (e.g., —C(C=O)—CH$_2$— for —C(C=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, 7:267-357, "Peptide and Backbone Modifications," Marcel Decker, NY).

As discussed, a peptide can be characterized as a mimetic by containing one or more non-natural residues in place of a naturally occurring amino acid residue. Non-natural residues are known in the art. Particular non-limiting examples of non-natural residues useful as mimetics of natural amino acid residues are mimetics of aromatic amino acids include, for example, D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenyl-phenylalanine; and D- or L-2-indole(alkyl)alanines, where alkyl can be substituted or unsubstituted methyl, ethyl, propyl, hexyl, butyl, pentyl, isopropyl, iso-butyl, sec-isotyl, iso-pentyl, or a non-acidic amino acid. Aromatic rings of a non-natural amino acid that can be used in place a natural aromatic ring include, for example, thiazolyl, thiophenyl, pyrazolyl, benzimidazolyl, naphthyl, furanyl, pyrrolyl, and pyridyl aromatic rings.

Cyclic peptides or cyclized residue side chains also decrease susceptibility of a peptide to proteolysis by exopeptidases or endopeptidases. Thus, certain embodiments embrace a peptidomimetic of the peptides disclosed herein, whereby one or more amino acid residue side chains are cyclized according to conventional methods.

Mimetics of acidic amino acids can be generated by substitution with non-carboxylate amino acids while maintaining a negative charge; (phosphono)alanine; and sulfated threonine. Carboxyl side groups (e.g., aspartyl or glutamyl) can also be selectively modified by reaction with carbodiimides (R'—N=C=N—R') including, for example, 1-cyclohexyl-3(2-morpholinyl-(4-ethyl) carbodiimide or 1-ethyl-3 (4-azonia-4,4-dimetholpentyl) carbodiimide. Aspartyl or glutamyl groups can also be converted to asparaginyl and glutaminyl groups by reaction with ammonium ions.

Lysine mimetics can be generated (and amino terminal residues can be altered) by reacting lysinyl with succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Methionine mimetics can be generated by reaction with methionine sulfoxide. Proline mimetics of include, for example, pipecolic acid, thiazolidine carboxylic acid, dehydroproline, 3- or 4-methylproline, and 3,3,-dimethylproline.

One or more residues can also be replaced by an amino acid (or peptidomimetic residue) of the opposite chirality. Thus, any amino acid naturally occurring in the L-configuration (which can also be referred to as R or S, depending upon the structure of the chemical entity) can be replaced with the same amino acid or a mimetic, but of the opposite chirality, referred to as the D-amino acid, but which can additionally be referred to as the R- or S-form.

As will be appreciated by one skilled in the art, the peptidomimetics of the present invention can also include one or more of the modifications described herein for derivatized peptides, e.g., a label, one or more post-translational modifications, or cell-penetrating sequence.

As with peptides of the invention, peptidomimetics are desirably 6 to 20 residues in length, or more desirably 7 to 15 residues in length. In certain embodiments, a selective inhibitor of the CFTR and CAL interaction is a 6 to 20 residue peptidomimetic based on the amino acid sequence of SEQ ID NO:1 or SEQ ID NO:24. In certain embodiments of the present invention, a selective inhibitor of the CFTR and CAL interaction is a peptidomimetic listed in Table 3.

TABLE 3

| Peptide Designation | Peptide Sequence | SEQ ID NO: |
|---|---|---|
| PRC 21 | WrFK(K-FITC)-ANSRWPTSII | 25 |
| PRC 23 | WrFKK-ANSRWPTSII | 26 |
| PRC 29 | WrFK(K-ROX)-ANSRWPTSII | 27 |
| PRC 37 | pneaWPTSII | 28 |
| B1 | fNaRWQTSII | 29 |
| B2 | fNSRWQTSII | 30 |
| B3 | knSRWQTSII | 31 |
| B4 | pnSRWQTSII | 32 |
| A6 | AnSRWQTSII | 33 |

Lower-case = D-amino acids; FITC = fluorescein; ROX = 6-carboxy-X-rhodamine.
Underlined residues indicate cyclized side chains.
WrFKK (SEQ ID NO: 34) is a cell penetrating peptide.

Also included with the scope of the invention are peptides and peptidomimetics that are substantially identical to a sequence set forth herein, in particular SEQ ID NO:1 or SEQ ID NO:24. The term "substantially identical," when used in reference to a peptide or peptidomimetic, means that the sequence has at least 75% or more identity to a reference sequence (e.g., 80%, 85%, 90%, 95%, 96%, 97%, 98%, 99%). The length of comparison sequences will generally be at least 5 amino acids, but typically more, at least 6 to 10, 7 to 15, or 8 to 20 residues. In one aspect, the identity is over a defined sequence region, e.g., the amino or carboxy terminal 3 to 5 residues.

The peptides, derivatives and peptidomimetics can be produced and isolated using any method known in the art. Peptides can be synthesized, whole or in part, using chemical methods known in the art (see, e.g., Caruthers (1980) *Nucleic Acids Res. Symp. Ser.* 215-223; Horn (1980) *Nucleic Acids Res. Symp. Ser.* 225-232; and Banga (1995) *Therapeutic Peptides and Proteins, Formulation, Processing and Delivery Systems*, Technomic Publishing Co., Lancaster, Pa.). Peptide synthesis can be performed using various solid-phase techniques (see, e.g., Roberge (1995) *Science* 269:202; Merrifield (1997) *Methods Enzymol.* 289:3-13) and automated synthesis may be achieved, e.g., using the ABI 431A Peptide Synthesizer (Perkin Elmer) in accordance with the manufacturer's instructions.

Individual synthetic residues and peptides incorporating mimetics can be synthesized using a variety of procedures and methodologies known in the art (see, e.g., *Organic Syntheses Collective Volumes*, Gilman, et al. (Eds) John Wiley & Sons, Inc., NY). Peptides and peptide mimetics can also be synthesized using combinatorial methodologies. Techniques for generating peptide and peptidomimetic libraries are well-known, and include, for example, multipin, tea bag, and split-couple-mix techniques (see, for example, al-Obeidi (1998) *Mol. Biotechnol.* 9:205-223; Hruby (1997) *Curr. Opin. Chem. Biol.* 1:114-119; Ostergaard (1997) *Mol. Divers.* 3:17-27; and Ostresh (1996) *Methods Enzymol.* 267:220-234). Modified peptides can be further produced by chemical modification methods (see, for example, Belousov (1997) *Nucleic Acids Res.* 25:3440-3444; Frenkel (1995) *Free Radic. Biol. Med.* 19:373-380; and Blommers (1994) *Biochemistry* 33:7886-7896).

Alternatively, peptides of this invention can be prepared in recombinant protein systems using polynucleotide sequences encoding the peptides. By way of illustration, a nucleic acid molecule encoding a peptide of the invention is introduced into a host cell, such as bacteria, yeast or mammalian cell, under conditions suitable for expression of the peptide, and the peptide is purified or isolated using methods known in the art. See, e.g., Deutscher et al. (1990) *Guide to Protein Purification: Methods in Enzymology* Vol. 182, Academic Press.

It is contemplated that the peptides and mimetics disclosed herein can be used as lead compounds for the design and synthesis of compounds with improved efficacy, clearance, half-lives, and the like. One approach includes structure-activity relationship (SAR) analysis (e.g., NMR analysis) to determine specific binding interactions between the agent and CAL or CFTR to facilitate the development of more efficacious agents. Agents identified in such SAR analysis or from agent libraries can then be screened for their ability to increase cell surface expression of CFTR.

In this regard, the present invention also relates to a method for identifying an agent for which facilitates cell surface expression of a degradation-prone CFTR. The method of the invention involves contacting CAL with a test agent under conditions allowing an interaction between the agent and CAL, and determining whether the agent competitively displaces binding of a degradation-prone CFTR to CAL. Particular degradation-prone CFTRs that can be used include, but are not limited to, ΔF508 and R1066C.

In one embodiment, the method is performed in vivo. Various detection methods can be employed to determine whether the agent displaces CFTR from CAL. For example, displacement can be based on detecting an increase in an amount of CFTR protein on the cell surface, immunostaining with a specific antibody (e.g., anti-CFTR, M3A7), or direct visualization (e.g., a CFTR-GFP fusion). Additional methods useful for determining whether there is an increase in cell surface protein included cell panning. In cell panning assays, plates are coated with an antibody that binds to the cell surface protein. The number of cells that binds to the antibody coated plate corresponds to an amount of protein on the cell surface.

In another embodiment, the method is performed in vitro. In accordance with this embodiment, a combination of peptide-array screening and fluorescence polarization is used to identify agents that bind to an isolated, recombinant CAL PZD domain. For example, it contemplated that the high-affinity CAL-binding peptides disclosed herein can be use as reporters for small-molecule screening assays, wherein the small molecules compete for binding to the CAL PZD domain. The ability to target PDZ proteins selectively, using a combination of peptide-array screening and fluorescence-polarization assays on purified, recombinant PDZ domains, represents a novel achievement, due to the bi-directional promiscuity of PDZ:protein interactions. Since PDZ proteins are implicated in the trafficking and intracellular localization of many disease-related receptors, selective targeting may provide an important tool for identifying additional PDZ-based therapeutics.

In so far as it is desirable that the agent selectively inhibit the interaction between CAL and CFTR, a further embodiment of this invention embraces contacting NHERF1 and/or NHERF2 with an identified inhibitor of the CAL and CFTR interaction and determining whether the agent competitively displaces binding to NHERF1 and/or NHERF2. Agents that fail to inhibit, or inhibit to a substantially lesser degree the interaction between CFTR and NHERF1 or NHERF2 as compared to CAL, would be considered selective.

Agents which can be screened in accordance with the methods disclosed herein can be from any chemical class including peptides, antibodies, small organic molecules, carbohydrates, etc.

Agents specifically disclosed herein, as well as derivatives, and peptidomimetics of said agents and agents identified by design and/or screening assays find application in increasing in the cell surface expression of degradation-prone CFTR proteins and in the treatment of CF. Thus, methods for increasing the cell surface expression of a degradation-prone CFTR and treating cystic fibrosis are also provided by this invention.

In accordance with one embodiment, the cell surface expression of a degradation-prone CFTR protein is enhanced or increased by contacting a cell expressing a degradation-prone CFTR with an agent that decreases or inhibits the interaction between the CFTR protein and CAL so that the cell surface expression of the CFTR protein is increased or enhanced. Desirably, the agent is administered in an amount that effectively stabilizes the degradation-prone CFTR protein and increases the amount of said CFTR protein present or detectable at the cell surface by at least 60%, 70%, 80%, 90%, 95%, 99% or 100% as compared to cells not contacted with the agent. Any cell can be employed in this method of the invention so long as it expresses a degradation-prone CFTR. Specific examples of such cells include, but are not limited to, primary cells of a subject with CF or cultured airway epithelial cell lines derived from a CF patient's bronchial epithelium (e.g., CFBE41O-). It is contemplated that this method of the invention can be used to increase cell surface expression of a degradation-prone CFTR protein in a human subject as well as increase the cell surface expression of a degradation-prone CFTR protein in an isolated cell or cell culture to, e.g., study the transport and/or activity of the mutant protein at the cell surface.

In another embodiment, a subject with CF or at risk of CF is treated with one or more the agents of the invention. In accordance with this embodiment, an effective amount of an agent that selectively inhibits the interaction between a degradation-prone CFTR and CAL is administered to a subject in need of treatment thereby preventing or treating the subject's cystic fibrosis. Subjects benefiting from treatment with an agent of the invention include subjects confirmed as having CF, subjects suspected of having CF, or subjects at risk of having CF (e.g., subjects with a family history).

Cystic Fibrosis is known to result from the dysfunction of CFTR due to mutations in the gene. While the most common mutations involve a deletion of phenylalanine in position 508, other mutations have been described (Grasemann & Ratjen (2010) *Expert Opin. Emerg. Drugs.* 15:653-659; Pettit & Johnson (2011) *Ann. Pharmacother.* 45:49-59) These can be classified according to the effect they have on the CFTR (Table 4). In one aspect, the subject, benefiting from treatment in accordance with the present invention expresses a degradation-prone CFTR (Class II mutation), such as ΔF508, ΔI507 or N1303K.

TABLE 4

| Class | Description |
|-------|-------------|
| I | Defective or absence of CFTR protein synthesis with premature termination of CFTR production |
| II | Impaired processing: typically a defect in protein trafficking and degradation by the endoplasmic reticulum |
| III | Defective regulation: the CFTR reaches the apical cell surface but is not activated by ATP or cAMP |
| IV | Impaired function: transport of chloride ions is reduced at the apical membrane |
| V | Reduced synthesis of normal functioning CFTR |

Jones & Helm (2009) Drugs 69: 2003-2010; Grasemann & Ratjen (2010) supra; O'Sullivan & Freedman (2009) Lancet 373: 1991-2004.

Successful clinical use of a selective inhibitor of the invention can be determined by the skilled clinician based upon routine clinical practice, e.g., by monitoring frequency of respiratory infections and/or coughing; or changes in breathing, abdominal pain, appetite, and/or growth according to methods known in the art.

Agents disclosed herein can be employed as isolated and purified molecules (i.e., purified peptides, derivatives, or peptidomimetics), or in the case of peptides, be expressed from nucleic acids encoding said peptides. Such nucleic acids can, if desired, be naked or be in a carrier suitable for passing through a cell membrane (e.g., DNA-liposome complex), contained in a vector (e.g., plasmid, retroviral vector, lentiviral, adenoviral or adeno-associated viral vectors and the like), symptoms of cystic fibrosis. Other agents of use in the combination therapy include, but are not limited to CFTR correctors, CFTR potentiators, mucolytics and anti-inflammatory agents.

CFTR correctors are molecules that correct one or more defects found in Class II mutations by rescuing proteins from endoplasmic reticulum degradation, improving trafficking of CFTR to the cell surface, and/or inhibiting proteins that are involved in the recycling of CFTR in the cell membrane. Several correctors have been identified using high throughput assays (O'Sullivan & Freedman (2009) *Lancet* 373:1991-2004). For example, Ataluren (3-[5-(2-Fluorophenyl)-1,2,4-oxadiazol-3-yl]benzoic acid) can cause ribosomal readthrough of premature stop mutations in patients with class I mutations, correct the processing of CFTR, and thereby increase the production of functional CFTR (Jones & Helm (2009) supra; Wilschanski, et al. (2011) *Eur. Respir. J.* 38:59-69). Lumacaftor (VX-809; 3-{6-{[1-(2,2-difluoro-1,3-benzodioxol-5-yl)cyclopropanecarbonyl]amino}-3-methylpyridin-2-yl}benzoic acid) is another corrector that acts as a "chaperone" to assist the movement of defective CFTR to the epithelial cell membrane (Jones & Helm (2009) supra; O'Sullivan & Freedman (2009) supra). Indeed, it has been shown that Lumacaftor can restore the $P_o$ of ΔF508-CFTR to near wild-type levels (Van Goor, et al. (2011) supra). Lumacaftor can be provided in any suitable form including, but not limited to tablet, capsule, injectable, or aerosol. Dosing of Lumacaftor can be in the range of 200 to 600 mg once daily. Another corrector is corr-4a (N-(2-(5-Chloro-2-methoxy-phenylamino)-4'-methyl-[4,5']bithiazolyl-2'-yl)-benzamide), which increases F508Δ-CFTR cell-surface expression and increases chloride conductance. As demonstrated herein, iCAL36 peptide can enhance therapeutic efficacy of correctors such as corr-4a.

A CFTR potentiator enhances the activity of CFTR that is correctly located at the cell membrane. CFTR potentiators are particularly useful in the treatment of subjects with class III mutations. CFTR potentiators of use in this invention include certain flavones and isoflavones, such as genistein, which are capable of stimulating CFTR-mediated chloride transport in epithelial tissues in a cyclic-AMP independent manner (See U.S. Pat. No. 6,329,422, incorporated herein by reference in its entirety); phenylglycine-01 (2-[(2-1H-indol-3-yl-acetyl)-methylamino]-N-(4-isopropylphenyl)-2-phenylacetamide); felodipine (Ethyl methyl 4-(2,3-dichlorophenyl)-2,6-dimethyl-1,4-dihydro-3,5-pyridinedicarboxylate); sulfonamide SF-01 (6-(ethylphenylsulfamoyl)-4-oxo-1,4-dihydroquinoline-3-carboxylic acid cycloheptylamide); and UCCF-152 (3-[2-(benzyloxy)phenyl]-5-(chloromethyl)isoxazole). Ivacaftor (VX-770; N-(2,4-Di-tert-butyl-5-hydroxyphenyl)-4-oxo-1,4-dihydroquinoline-3-carboxamide) has also been shown to increase CFTR channel open probability ($P_o$) in both the F508Δ processing mutation and the G551D gating mutation (Van Goor, et al. (2011) supra). Ivacaftor can be provided, e.g., in tablet form (KALYDECO; 150 mg Ivacaftor) or alternatively in any other suitable form, e.g., as an aerosol, capsule or injectable. Dosing of Ivacaftor can, e.g., include 250 mg Ivacaftor every 12 hours.

In some embodiments, the other agent is a single compound with dual corrector and potentiator activities. Such agents include VRT-532 (3-(2-hydroxy-5-methylphenyl)-5-phenylpyrazole) and cyanoquinolines such as N-(2-((3-Cyano-5,7-dimethylquinolin-2-yl)amino)ethyl)-3-methoxybenzamide (CoPo-2), as well as hybrid bithiazole-phenylglycine corrector-potentiators which, when cleaved by intestinal enzymes, yield an active bithiazole corrector and phenylglycine potentiator (Mills, et al. (2010) *Bioorg. Med. Chem. Lett.* 20:87-91).

Mucolytics are agents that dissolve thick mucus by dissolving various chemical bonds within secretions, which in turn can lower the viscosity by altering the mucin-containing components. Mucolytics of use in this invention include, but are not limited to acetylcysteine ((2R)-2-acetamido-3-sulfanylpropanoic acid), ambroxol (trans-4-(2-Amino-3,5-dibrombenzylamino)-cyclohexanol), bromhexine (2,4-dibromo-6-{[cyclohexyl(methyl)amino]methyl}aniline), carbocisteine (R)-2-Amino-3-(carboxymethylsulfanyl)propanoic acid), domiodol ([2-(iodomethyl)-1,3-dioxolan-4-yl] methanol), dornase alfa (recombinant human deoxyribonuclease I), eprazinone (3-[4-(2-ethoxy-2-phenyl-ethyl) piperazin-1-yl]-2-methyl-1-phenyl-propan-1-one), erdosteine (2-[(2-oxothiolan-3-yl)carbamoylmethylsulfanyl] acetic acid), letosteine (2-{2-[(2-ethoxy-2-oxoethyl)thio] ethyl}-1,3-thiazolidine-4-carboxylic acid), mannitol, mesna (sodium 2-sulfanylethanesulfonate), neltenexine (N-(2,4-dibromo-6-{[(4-hydroxycyclohexyl)amino]methyl}phenyl) thiophene-2-carboxamide), and sobrerol ((1S)-5-(1-hydroxy-1-methylethyl)-2-methylcyclohex-2-en-1-ol), stepronin (N-{2-[(2-thienylcarbonyl)thio] propanoyl}glycine).

Inflammation is a major component of cystic fibrosis. If untreated, inflammation can irreversibly damage the airways, leading to bronchiectasis and ultimately respiratory failure. Anti-inflammatory drugs used in the treatment of cystic fibrosis include steroids such as corticosteroids and nonsteroidal anti-inflammatory drugs such as ibuprofen. Other agents include pentoxifylline and azithromycin, which, in addition to its antimicrobial effects, also possesses anti-inflammatory properties.

Other therapeutics of use in combination with the agents of this invention include, but are not limited to, 2,2-dimethyl butyric acid (U.S. Pat. No. 7,265,153); glycerol, acetic acid, butyric acid, D- or L-amino-n-butyric acid, alpha- or beta-amino-n-butyric acid, arginine butyrate or isobutyramide, all disclosed in U.S. Pat. Nos. 4,822,821 and 5,025,029; and butyrin, 4-phenyl butyrate, phenylacetate, and phenoxy acetic acid, disclosed in U.S. Pat. No. 4,704,402.

The combination therapy of this invention preferably includes (a) at least one agent that selectively inhibits the interaction between a degradation-prone CFTR and CAL and (b) a CFTR corrector, CFTR potentiator, mucolytic, anti-inflammatory agent, or combination thereof. In some embodiments, the combination therapy of this invention includes (a) at least one agent that selectively inhibits the interaction between a degradation-prone CFTR and CAL and (b) a CFTR corrector, CFTR potentiator, or combination thereof. In accordance with this invention, the active agents of the combination therapy can be administered simultaneously of consecutively, within seconds, minutes, hours, days or weeks of each other. It is expected that the above-referenced combination therapy will have an additive or synergistic effect in the treatment of cystic fibrosis. In particular, it is expected that the combination of a selective inhibitor of the CFTR and CAL interaction, a CFTR corrector, and a CFTR potentiator will reverse all three defects (folding, gating, and stability) of ΔF508-CFTR.

The present invention also provides a kit containing (a) an agent for inhibiting the interaction between a degradation-prone CFTR and CAL in combination with (b) a CFTR corrector, CFTR potentiator, mucolytic, anti-inflammatory agent, or combination thereof, for use in the prevention or treatment of cystic fibrosis. In some embodiments, the kit includes a plurality of separate containers, each containing at least one active agent useful in a combination therapy for the prevention or treatment of cystic fibrosis. The kit contains a first container containing an agent for inhibiting the interaction between a degradation-prone CFTR and CAL. The kit further includes a container for a CFTR corrector, a container for a CFTR potentiator, a container for a mucolytic, and or a container for an anti-inflammatory agent. The containers of the kit may be enclosed within a common outer packaging, such as, for example a cardboard or plastic box or a shrink wrap outer skin enclosing the various containers. In certain embodiments, the agent for inhibiting the interaction between a degradation-prone CFTR and CAL; and CFTR corrector, CFTR potentiator, mucolytic, and/or anti-inflammatory agent are each individually formulated in an acceptable carrier. The kit may be in the form of a consumer package or prescription package which provides the products described above. The package may provide instructions or directions on how to use and/or combine the products for one or more treatment regimens.

For therapeutic use, active agents of the invention can be formulated with a pharmaceutically acceptable carrier at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and anti-oxidants can also be present in the compositions.

Compositions of the present invention can be administered parenterally (for example, by intravenous, intraperitoneal, subcutaneous or intramuscular injection), topically including via inhalation, transdermally, orally, intranasally, intravaginally, or rectally according to standard medical practices.

The selected dosage level of an agent will depend upon a variety of factors including the activity of the particular agent of the present invention employed, the route of administration, the time of administration, the rate of excretion or metabolism of the particular agent being employed, the duration of the treatment, other drugs, compounds and/or materials used in combination with the particular agent employed, the age, sex, weight, condition, general health and prior medical history of the patient being treated, and other factors well-known in the medical arts.

A physician having ordinary skill in the art can readily determine and prescribe the effective amount of the pharmaceutical composition required based upon the administration of similar compounds or experimental determination. For example, the physician could start doses of an agent at levels lower than that required in order to achieve the desired therapeutic effect and gradually increase the dosage until the desired effect is achieved. This is considered to be within the skill of the artisan and one can review the existing literature on a specific agent or similar agents to determine optimal dosing.

The fact that other proteins destined for the intracellular transport pathway frequently exhibit transport delays due to mutations, or other factors, indicates that the cell-surface expression of such degradation-prone proteins may also be mediated by CAL. Thus, it is contemplated that the agents of this invention can also be used to induce or increase the cell surface expression of other degradation-prone proteins. Accordingly, physiological disorders associated with other degradation-prone proteins besides CFTR can similarly be treated using the methods disclosed herein. Physiological disorders associated with a degradation-prone protein that can be treated in a method of the invention include, for example, Stargardt's disease and particular types of macular dystrophy caused by mutations of the retinal rod transporter, ABC-R, resulting in deficiency of export.

The invention is described in greater detail by the following non-limiting examples.

Example 1

Materials and Methods

Protein Expression and Purification.

CALP (UniProt Accession No. Q9HD26-2) was expressed and purified (Cushing, et al. (2008) *Biochemistry* 47:10084-10098). TIP-1 (Accession No. O14907) was expressed and purified similarly except that an N-terminal $His_{10}$ tag was used with a HRV 3C protease recognition sequence (LEVLFQ*G; SEQ ID NO:35) upstream of the full-length protein sequence. Following TIP-1 purification via immobilized metal-affinity chromatography, the protein was injected onto a SUPERDEX S75 gel filtration column (GE Healthcare) equilibrated in 50 mM Tris pH 8.5, 150 mM NaCl, 0.1 mM TCEP, 0.02% $NaN_3$. Human rhinovirus 3C protease (Novagen) was added to the protein at a 1:30 mass ratio and incubated at 4° C. for 48 hours. Following cleavage, the protein was passed through a 1 mL HISTRAP HP column (GE Healthcare) equilibrated in 20 mM imidazole, 25 mM Tris pH 8.5, 150 mM NaCl, 0.1 mM TCEP, 0.02% $NaN_3$. The protein was further purified on a SUPERDEX S75 column as described above. Following gel filtration, the protein was dialyzed into gel filtration buffer with 5% glycerol. TIP-1 protein quantitation was achieved by using the $A_{280}$ nm experimentally determined extinction coefficient value of 10715 $cm^{-1}*M^{-1}$ (Cushing, et al. (2008) supra). All purified proteins were deemed thermally stable at the temperatures used for in vitro binding measurements by monitoring thermal stability (Cushing, et al. (2008) supra).

Peptide Synthesis.

All peptides, except those used in peptide arrays experiments, were synthesized and HPLC-purified by Tufts Peptide Core Facility. Peptides with N-terminally coupled fluorescein (via an aminohexanoic acid linker) are denoted by a "F*-" prefix. Biotin-conjugated peptides ("BT") were N-terminally coupled via an WrFKK (SEQ ID NO:34) linker sequence (r=D-Arg).

Cell Culture.

CFBE41o-cells (Bruscia, et al. (2002) *Gene Ther* 9:683-685) stably expressing ΔF508-CFTR under the control of a cytomegalovirus promoter (CFBE-ΔF cells; Li, et al. (2006) *Am. J. Respir. Cell Mol. Biol.* 34:600-608) are described in the art (Bebok, et al. (2005) *J. Physiol.* 569:601-615). Cells were cultured and switched to MEM containing only penicillin and streptomycin 24 hours before experiments. All cells used in experiments were between passages 15 and 20.

PDZ Pull-Down Assay.

Briefly, pull-down assays were performed by incubating biotin-conjugated peptides or buffer with streptavidin paramagnetic beads (PROMEGA). Excess peptide was removed by washing. Clarified CFBE-ΔF cell lysates were added to the beads and incubated with rotation for 90 minutes at 4° C. Beads were washed and bound proteins were eluted with buffer, peptide inhibitor, or scrambled peptide. Proteins were separated by SDS-PAGE and immunoblotted. For mass spectrometry identification, SILVERQUEST (Invitrogen) was used to silver stain protein bands according to manufacturer's instructions. Bands were considered to be candidate protein interactors if they were enriched in the specific non-biotinylated peptide-eluted lane (e.g. iCAL36) versus the SCR-eluted lane. Destained protein bands were identified. Confirmation of peptide fragments was from three independent sample submissions, with CAL and TIP-1 positively identified with each submission.

Fluorescence Anisotropy and Peptide Array Experiments.

Peptide fluorescence anisotropy binding studies were performed as described (Cushing, et al. (2008) supra). ΔΔG values were calculated from $K_i$ values. In the case of weak affinity inhibitors ($K_i$>1000 µM), $K_i$ values were estimated. Inverted peptide array experiments were performed as described (Boisguerin, et al. (2004) *Chem. Biol.* 11:449-459; Boisguerin, et al. (2007) *Chembiochem.* 8:2302-2307). For TIP-1 peptide array experiments, His$_{10}$ tagged (uncleaved) protein was used to facilitate quantitation.

TIP-1:iCAL36 Crystallization and Data Collection.

iCAL36 was added at a final concentration of 1 mM to purified TIP-1 at 5.5 mg ml$^{-1}$ in 10 mM HEPES pH 7.4, 25 mM NaCl. Initial crystallization conditions were identified for the TIP-1:iCAL36 complex by micro-batch screening at the Hauptman-Woodward Medical Research Institute High-Throughput Screening laboratory (Luft, et al. (2003) *J. Struct. Biol.* 142:170-179). Crystallization conditions identified by screening were optimized in hanging-drop format at 291 K, by adding 2 µl of the complex in screening buffer (5.5 mg ml$^{-1}$ TIP-1 and 1 mM iCAL36) to 2 µl reservoir solution. The reservoir contained 500 µl solution. Crystals appeared in 2-4 days and continued to grow for up to 14 days. The crystal used for data collection was obtained using 100 mM NH$_4$SCN, 100 mM MES pH 6.0, 36% (w/v) polyethylene glycol (PEG) 1000 as reservoir buffer.

For data collection, the crystal was transferred into cryoprotectant buffer [200 mM N$_{H4}$SCN, 100 mM MES pH 6.0, 30% (w/v) PEG 400. The data set used for structure determination was obtained at 100K, λ=1.0000 Å on beam line X6A at the National Synchrotron Light Source (NSLS) at Brookhaven National Laboratory. Two data sets were collected and later merged; one over a 360° range, using 0.3° frames and an exposure time of 2 seconds per frame, and the second over 60°, using 1° frames, an exposure time of 0.5 seconds per frame, and an aluminum foil filter. Diffraction data were processed using the XDS package. The TIP-1:iCAL36 complex crystallizes in space-group P1 with unit cell dimensions a=27.0, b=34.1, c=66.9 Å, α=79.6°, β=87.1°, γ=89.9°, and diffracted to a resolution of 1.24 Å.

TIP-1:iCAL36 Structure Determination and Refinement.

Molecular replacement was performed using PHENIX (Adams, et al. (2010) *Acta Crystallogr. D Biol. Crystallogr.* 66:213-221; McCoy, et al. (2007) *J. Appl. Crystallogr.* 40:658-674), using the TIP-1:β-catenin structure as a template (PDB ID=3DIW; Zhang, et al. (2008) *J. Mol. Biol.* 384:255-263). The model was built and refined using phenix (Adams, et al. (2010) supra). The final structure has a $R_{work}$=18.0% and $R_{free}$=19.3%. Detailed data collection and refinement statistics are in Table 5.

TABLE 5

| Data Collection | |
|---|---|
| Space Group | P1 |
| Unit cell dimensions: | |
| a, b, c (Å) | 26.97, 34.09, 66.86 |
| α, β, γ (°) | 79.64, 87.15, 89.97 |
| Matthews Coefficient (Å$^3$ Da$^{-1}$) | 2.01 |
| Molecules in ASU (Z) | 2 |
| Solvent content | 0.39 |
| Wavelength (Å) | 0.9181 |
| Resolution$^a$ (Å) | 19.11-1.24 (1.31-1.24) |
| Unique reflections | 60547 |
| $R_{sym}^b$ | 0.04 (0.27) |
| <I/σ$_I$> | 27.63 (4.29) |
| $R_{mrgd-F}^c$ | 5.5 (43.9) |
| Completeness (%) | 91.3 (70.0) |
| Molecular Replacement | |
| Rotation function search | |
| Peak no. | 0 |
| Log-likelihood gain | 191 |
| Z-score | 15.4 |
| Translation function search | |
| Peak no. | 2 |
| Log-likelihood gain | 749 |
| Z-score | 22.9 |
| Overall log-likelihood gain | 1476 |
| Refinement | |
| Total number of reflections | 60,539 |
| Reflections in the test set | 3,044 |
| $R_{work}^d$/$R_{free}^e$ | 0.180/0.193 |
| Number of atoms: | |
| Protein | 1,923 |
| Solvent | 256 |
| Ramachandran plot$^f$ (%) | 92.1/7.9/0/0 |
| B$_{av}$ (Å$^2$) | |
| Protein | 19.75 |
| Solvent | 28.01 |
| Bond length RMSD | 0.005 |
| Bond angle RMSD | 0.985 |

$^a$Values in parentheses are for data in the highest-resolution shell.
$^b$Rsym = Σhi |I(h) − Ii(h)|/hi Ii(h), where Ii(h) and I(h) values are the i-th and mean measurements of the intensity of reflection h, respectively.
$^c$SigAno = <(|F(+) − F(−)|/σ$_A$)>.
$^d$Rwork = Σh |Fobs(h) − Fcalc(h)|/Σh Fobs(h), hε {working set}.
$^e$Rfree = h _Fobs(h) _ Fcalc(h)_/h Fobs(h), hε {test set}.
$^f$Core/allowed/generously allowed/disallowed.

TIP-1:iCAL42 and TIP-1:β-Catenin Substitution Modeling.

The TIP-1:iCAL36 and TIP-1:β-catenin structures were aligned using PyMOL (RMSD=0.38 Å).

TIP-1:β-Catenin Substitution Modeling.

The TIP-1:β-catenin cocrystal structure (PDB ID=3DIW; Zhang, et al. (2008) supra) was used as a template for assessing the observed loss of affinity in the iCAL42 Trp-Leu P$^{-5}$ ligand substitution. The P$^{-5}$ tryptophan was substituted for leucine in WINCOOT (Emsley, et al. (2010) *Acta Crystallogr. D Biol. Crystallogr.* 66:486-501), and individual PDB files created for the possible rotomers. Each rotamer was evaluated for potential steric clashes and non-optimal bond geometry with MOLPROBITY (Chen, et al. (2010) *Acta Crystallogr. D Biol. Crystallo Ussing Chamber gr.* 66:12-21).

Measurements.

Short circuit current ($I_{SC}$) measurements were performed. Briefly, 10$^5$ cells were seeded onto 12 mm SNAPWELL permeable supports (Corning) and allowed to form polarized monolayers over the course of 9 days. CFBE-ΔF cells were dosed with 0.5 mM peptide via BIOPORTER (Sigma) 3.5 hour before the start of Ussing chamber measurements. Cells were maintained at 37° C. throughout treatments; the DMSO concentration did not exceed 0.03%. Cells were treated sequentially with 50 μM amiloride, 20 μM forskolin, 50 μM genistein, and 5 μM CFTR$_{inh}$-172 in 5.0 minute intervals. CFTR-specific chloride efflux was computed as the magnitude of $\Delta I_{SC}$ following application of CFTR$_{inh}$-172. Resistances were monitored throughout each experiment to ensure monolayer integrity.

Statistical Analysis.

Values are reported as mean±SD except for Ussing chamber experiments where mean±SEM is reported. Student's one-tailed t-test was used for fluorescence anisotropy binding experiments while the Student's one-tailed paired t-test was used for analysis of Ussing chamber experiments.

Computational Designs with K*.

The previously-determined NMR structure of the CAL PDZ domain bound to the C-terminus of CFTR was used to model the binding of CAL to CFTR (Piserchio, et al. (2005) *Biochemistry* 44:16158-16166). The CFTR peptide in the NMR structure was truncated to the six most C-terminal amino acids and mutated to the amino acid sequence WQTSII (SEQ ID NO:36) to mimic the best peptide hexamer for CAL discovered thus far. An acetyl group was modeled onto the N-terminus of the peptide using restrained molecular dynamics and minimization where the N-terminus of the peptide was allowed to move, while the remainder of the protein complex was restrained using a harmonic potential (Case, et al. (2005) *J. Comp. Chem.* 26:1668-1688). An 8 Å shell around the peptide hexamer was used as the input structure to K*. The four most C-terminal residues, TSII (SEQ ID NO:37), were allowed to mutate to the following residues during the design search: Thr (all amino acids except Pro), Ser (T/S), Ile (all amino acids except Pro), and Ile (I/L/V). In addition, the Probe program (Word, et al. (1999) *J. Mol. Biol.* 285:1711-1733) was used to determine the side-chains on CAL that interact with the CFTR peptide mimic. The nine residues that interact with the peptide, as well as the two most N-terminal residues on the peptide, were allowed to be flexible during the design search. The peptide was allowed to rotate and translate as a rigid body during the search, as previously described for small molecules (Chen, et al. (2009) supra; Georgiev, et al. (2008) supra; Frey, et al. (2010) *Proc. Natl. Acad. Sci. USA* 107:13707-13712). To explore the feasibility of the new algorithms, unless otherwise noted, full partition functions were not computed and a maximum of $10^3$ conformations were allowed to contribute to each partition function.

Peptide Array Comparison.

The peptide array data was composed of 6223 C-termini (11-mers) from human proteins. The array was incubated with the CAL PDZ domain in order to determine binding of CAL to the 11-mers. The K* algorithm was used to evaluate 4-mer structural models of the peptide-array sequences to verify the accuracy of the predictions.

To compare the array data with the K* predictions, the quantitative array data, measured in biochemical light units (BLUs), was converted into a binary yes/no CAL binding event. In other words, by setting a binding cutoff on the peptide array, each sequence was classified as either a CAL binder or non-binder. The cutoff value was chosen as three standard deviations away from the average BLU value of the array.

Prospective Computational Predictions.

K* was used to search over all peptide sequences within the CAL PDZ domain sequence motif to find new CAL peptide inhibitors. For computational efficiency, the number of conformations enumerated by A* for each partition function was limited to $10^3$ conformations. Two sets of peptides (promising designs and poorly ranked designs) were chosen to be experimentally validated.

In order to choose the most promising peptide inhibitors, a second K* design was performed, where K* scores for the top 30 sequences were re-calculated with the number of enumerated conformations per partition function increased to $10^5$. Several top-ranked sequences were chosen to be experimentally tested. First, the top seven ranked sequences from the second run were chosen. In addition, two sequences that greatly increased in ranking from the first to second run (rank 29 to 9, and rank 28 to 11) were chosen as well. Finally, a K* run was conducted using Charmm forcefield parameters instead of Amber parameters. Two sequences that scored high on both the Amber and Charmm runs were chosen to be experimentally tested as well.

The poorly-ranked designs were chosen to minimize the sequence similarity among the set of poorly-ranked peptides. First, the worst-ranked peptide was chosen and added to initialize the set of negative sequences. Next, sequences were successively chosen from the worst 200 K* ranked sequences and added to the set in order to maximize the amino acid sequence diversity with all the sequences already in the set. The similarity between two sequences was determined using the PAM-30 similarity matrix (Dayhoff, et al. (1978) *Nat. Biomed. Res. Found.* 5:345-352). In total, 23 (eleven top-ranked and twelve poorly-ranked) K*-computed peptide inhibitor sequences were experimentally tested.

Experimental Procedure.

The experimental inhibitory constants of top- and poorly-ranked peptide sequences from the K* CAL-CFTR design were experimentally determined. As a control, the best known peptide hexamer was also retested. The corresponding N-terminally acetylated peptides were purchased from NEO BioScience (Cambridge, Mass.) and the $K_i$ values for the peptides were detected using fluorescence polarization. Briefly, the CAL PDZ domain was incubated with a labeled peptide of known binding affinity. Each peptide inhibitor was serially diluted and the protein-peptide mixture was added to each dilution. Finally, the amount of competitive inhibition was tracked using residual fluorescence polarization.

The Ussing chamber experiments were performed as described herein. Polarized monolayers of patient-derived bronchial epithelial cells, CFBE-Δ cells, were treated with peptide and BIOPORTER (Gene Therapy Systems; San Diego, Calif.) delivery agent. Peptide inhibitor was applied to the monolayer and the short circuit currents ($I_{SC}$) were monitored in Ussing chambers. ΔF508-CFTR chloride flux was measured as the change in $I_{SC}$ when the CFTR specific inhibitor, CFTR$_{inh}$-172 (Taddel, et al. (2004) *FEBS let.* 558:52-56; Ma, et al. (2002) *J. Clin. Invest.* 110:1651-1658), was applied to the cell monolayer.

Example 2

Identification of Selective Inhibitors of the CAL and CFTR Interaction

Using peptide-array screening and fluorescence-polarization binding assays, a series of peptide sequences were identified that bind CAL progressively more tightly than CAL binds to CFTR, and that in parallel bind NHERF1 and NHERF2 progressively more weakly than these proteins bind to CFTR.

To test the ability of CAL inhibitors to rescue CFTR, cultured airway epithelial cells (cell line CFBE41o-, derived from a CF patient's Bronchial Epithelium) were grown on filters, permitting formation of polarized cell monolayers similar to those found in epithelial tissues. The CFBE41o-cell line is well-recognized as an airway epithelial model system for the study of CF processes. These cells express the most common disease mutant associated with CF, ΔF508-CFTR, which is characterized by the loss of a single amino acid codon at position 508 of CFTR. Roughly 50% of CF patients are homozygous for ΔF508-CFTR, and another 40% are heterozygotes for this allele. Functional rescue of ΔF508-CFTR therefore has the potential to alleviate symptoms in up to 90% of CF patients. Although very little ΔF508-CFTR protein is synthesized in the absence of intervention, the protein itself retains some functional activity. If rescued and stabilized it can restore physiological CFTR activity, potentially reversing the processes that lead to chronic lung infection, and ultimately death, in most CF patients.

When introduced into CFBE41o-cells using commercial peptide transfection reagents, representative peptide and peptidomimetic compounds were able to increase the amount of ΔF508-CFTR protein at the apical membrane and to increase the CFTR-mediated chloride efflux across the monolayers. The magnitude of the functional rescue correlated with the selectivity of the peptides for CAL vs. NHERF1 and NHERF2; the more selective the peptide for the CAL binding site, the more effective it was at enhancing chloride efflux.

Furthermore, when used in combination with a compound that enhances the biosynthesis of ΔF508-CFTR (a "corrector"), the instant inhibitors showed an additive effect, comparable in magnitude to that of the corrector compound.

Although compounds have previously been designed to enhance the synthesis and/or chloride-channel activity of CFTR, the instant inhibitors were designed to stabilize mutant CFTR protein that has already been synthesized within the cell and successfully transported to the cell surface. The peptides and peptidomimetics disclosed herein provide a basis for further optimization of CAL inhibitor properties in terms of affinity and selectivity for CAL, in vivo proteolytic stability, cellular uptake, and ADME characteristics.

Example 3

Assays for Assessing Activity of Selective Inhibitors

Agents of the present invention can be assayed for their ability to stimulate chloride transport in epithelial tissues. Such transport may result in secretion or absorption of chloride ions. The ability to stimulate chloride transport may be assessed using any of a variety of systems. For example, in vitro assays using a mammalian trachea or a cell line, such as the permanent airway cell line Calu-3 (ATCC Accession Number HTB55) may be employed. Alternatively, the ability to stimulate chloride transport may be evaluated within an in vivo assay employing a mammalian nasal epithelium. In general, the ability to stimulate chloride transport may be assessed by evaluating CFTR-mediated currents across a membrane by employing standard Ussing chamber (see Ussing & Zehrahn (1951) Acta. Physiol. Scand. 23:110-127) or nasal potential difference measurements (see Knowles, et al. (1995) Hum. Gene Therapy 6:445-455). Within such assays, an agent that stimulates a statistically significant increase in chloride transport at a concentration of about 1-300 µM is said to stimulate chloride transport.

Within one in vitro assay, the level of chloride transport may be evaluated using mammalian pulmonary cell lines, such as Calu-3 cells, or primary bovine tracheal cultures. In general, such assays employ cell monolayers, which may be prepared by standard cell culture techniques. Within such systems, CFTR-mediated chloride current may be monitored in an Ussing chamber using intact epithelia. Alternatively, chloride transport may be evaluated using epithelial tissue in which the basolateral membrane is permeabilized with Staphylococcus aureus α-toxin, and in which a chloride gradient is imposed across the apical membrane (see Illek, et al. (1996) Am. J. Physiol. 270:C265-75). In either system, chloride transport is evaluated in the presence and absence of a test agent, and those compounds that stimulate chloride may be used within the methods provided herein.

Within another in vitro assay for evaluating chloride transport, cells, such as NIH 3T3 fibroblasts, are transfected with a CFTR gene having a mutation associated with cystic fibrosis (e.g., ΔF508-CFTR) using well known techniques (see Anderson, et al. (1991) Science 25:679-682). The effect of an agent on chloride transport in such cells is then evaluated by monitoring CFTR-mediated currents using the patch clamp method (see Hamill, et al. (1981) Pflugers Arch. 391:85-100) with and without agent.

Alternatively, such assays may be performed using a mammalian trachea, such as a primary cow tracheal epithelium using the Ussing chamber technique as described above. Such assays are performed in the presence and absence of a test agent to identify agents that stimulate chloride transport.

Example 4

Single-Domain Specificity of a CAL PDZ Inhibitor that Rescues ΔF508-CFTR iCAL36 is a Highly Selective PDZ Inhibitor.

To determine the full spectrum of PDZ domains inhibited by iCAL36 (sequence: ANSRWPTSII; SEQ ID NO:20) in epithelial cells, a pull-down/mass-spectrometry assay for iCAL36 interactors was developed. As bait, an N-terminally biotinylated (BT-) version of iCAL36 was used, which retained the binding profile of the decamer. BT-iCAL36 was coupled to streptavidin beads and incubated with whole-cell lysates (WCL) from human cystic fibrosis bronchial epithelial cells expressing ΔF508-CFTR (CFBE-ΔF cells). Mass spectrometry revealed only two PDZ proteins among the "prey" proteins that were enriched in iCAL36 vs. control eluates. CAL was identified with good peptide coverage. The second PDZ sequence identified by mass-spectrometry was the Tax-interacting protein-1 (TIP-1). Both interactions were validated using WCL pull-downs and immunoblot analysis. Thus, although initially engineered to avoid interactions only with the NHERF1 and NHERF2 PDZ domains, iCAL36 has a strikingly selective interaction profile, robustly engaging only a single "off-target" protein among the entire spectrum of PDZ proteins present in airway epithelial cell lysates.

The significant enrichment of the iCAL36-eluted bands over the inputs, especially in the case of TIP-1, was consistent with a potent interaction. To quantify its strength relative to the on-target binding of CAL, recombinant expression and purification protocols were developed for the TIP-1 PDZ domain and its interaction with a fluoresceinated iCAL36 peptide (F*-iCAL36) was monitored by means of fluorescence polarization (FP). Titration revealed a strong, dose- and sequence-dependent binding isotherm, with a fitted $K_d$ of 0.54 µM. Surprisingly, TIP-1 actually bound F*-iCAL36 2.5-fold more tightly than CAL ($K_d$=1.3 µM), and its submicromolar interaction placed it at the high-affinity end of the spectrum of PDZ:peptide interactions (Stiffler et al. (2007) *Science* 317:364-369).

An unusual protein composed almost entirely of a single PDZ domain, TIP-1 has been implicated in negatively regulating the Wnt signaling pathway by sequestering β-catenin (Kanamori, et al. (2003) *J. Biol. Chem.* 278:38758-38764). Recent reports also suggest TIP-1 may play a role in regulating the surface expression of membrane proteins, including Kir 2.3 (Alewine, et al. (2006) *Mol. Biol. Cell* 17:4200-4211). Thus, despite the excellent overall specificity of iCAL36, its off-target interaction with TIP-1 could potentially have contributed to its effects on CFTR stability. To resolve this target ambiguity, and to test the ability to achieve true single-PDZ specificity, CAL inhibitors were designed without TIP-1 affinity.

Sequence Determinants of the iCAL36:TIP-1 Interaction.

As a basis for eliminating the off-target interaction, parallel structural and biochemical approaches were undertaken to understand the contributions of individual iCAL36 side chains to TIP-1 binding. To visualize the stereochemistry of binding, the structure of the TIP-1:iCAL36 complex was determined by X-ray crystallography. The iCAL36 peptide adopted a canonical PDZ-binding conformation in the TIP-1 binding pocket, with standard C-terminal carboxylate, $P^0$ and $P^{-2}$ interactions. In addition, the $P^{-5}$ side chain was bound within a deep, hydrophobic pocket that provided excellent stereochemical complementarity to the planar Trp-conjugated ring system. In contrast, the structure of the CAL PDZ domain showed no equivalent pocket.

In order to assess the free-energy contribution of each side chain to the interaction, substitutional analysis (SubAna) was performed by synthesizing peptide arrays containing the iCAL36 sequence with the amino acid at each position individually replaced with all 19 natural alternatives. Consistent with the stereochemistry of the interaction, the binding patterns of the CAL and TIP-1 PDZ domains also highlighted the importance of the $P^{-5}$ Trp side chain to the off-target binding affinity of iCAL36. $P^{-5}$ substitution with any other natural amino acid abrogated TIP-1 binding, whereas multiple substitutions were tolerated at other positions along the iCAL36 sequence. In contrast, CAL binding was retained for multiple substitutions at both the $P^{-5}$ position and elsewhere in the sequence. Both the biochemical and structural data thus indicated that the affinity of TIP-1 for iCAL36 was tightly focused on the $P^{-5}$ position, whereas CAL's affinity was more broadly distributed along the length of the peptide.

To identify the sources of iCAL36 affinity for TIP-1 in more detail, the TIP-1 binding affinity of the somatostatin receptor subtype 5 (SSR5) C-terminal peptide (ANGLMQTSKL; SEQ ID NO:38) was also determined, which was the starting sequence for the original peptide engineering effort. Using F*-iCAL36 as a high-affinity reporter peptide, an FP displacement assay revealed that the SSR5 sequence interacted with TIP-1 even though it had a Met at the $P^{-5}$ position, a substitution that abrogated TIP-1 binding in the context of the iCAL36 sequence. In comparison to unlabeled iCAL36, which binds TIP-1 with a $K_i$ of 1.8 μM, the $K_i$ for the unlabeled SSR5 peptide binding was 130 μM. Taken together, these data indicate that both the baseline affinity of the SSR5 starting sequence and the $P^{-5}$ Trp represented potential contributors to the high affinity of the off-target interaction.

A Stereochemical Achilles' Heel.

The ability of the combinatorial peptide-array/FP counter-screening paradigm to improve the iCAL selectivity profile was analyzed. CombLib peptide arrays, in which all 400 possible pairs of amino acids were inserted into positions $P^{-5}$ and $P^{-4}$ had already been evaluated for binding to the CAL and NHERF PDZ domains as described herein. A comparable CombLib was subsequently prepared and surveyed for TIP-1 binding. In the framework of the iCAL36 sequence, TIP-1 binding was strictly confined to peptides that included an aromatic residue at $P^{-5}$. Parallel CombLibs based on the full iCAL36 sequence confirmed that the $P^{-5}$ and $P^{-4}$ preferences were relatively independent of upstream sequence context.

Comparison with published arrays identified a number of combinations that bound CAL, but did not bind TIP-1 or any of the NHERF domains studied. Among these was a Leu/Pro combination. The SubAna arrays showed that the CAL-binding signal of the $P^{-5}$ Leu substitution was comparable to those of the strongest Trp/Xaa combinations. Separate SubAna arrays based on the new sequence (iCAL42; ANSRLPTSII; SEQ ID NO:21) confirmed that the CAL PDZ binding preferences were largely retained. Underscoring the critical contribution of the $P^{-5}$ Trp side chain, TIP-1 binding was abrogated for all single substitutions of the Leu-based iCAL42 sequence except for the Leu/Trp revertant.

In order to quantitate the impact of the $P^{-5}$ Leu substitution and to assess inhibitory potential at high peptide concentrations, FP displacement assays were performed. Consistent with the qualitative data, CAL displacement isotherms showed that iCAL42 retained robust CAL PDZ affinity, with a fitted $K_i$ value of 53 μM, only three-fold weaker than unlabeled iCAL36. The NHERF CombLib preferences were also validated: iCAL42 failed to bind any of the four NHERF1 or NHERF2 PDZ domains with appreciable affinity. Critically, the iCAL42 displacement isotherm for TIP-1 was also essentially indistinguishable from the vehicle control up to millimolar peptide concentrations, representing a >1500-fold decrease in binding affinity. Thus, in the context of the iCAL36 sequence, the $P^{-5}$ side chain acted as a single-site TIP-1 affinity switch.

Compared to the >1500-fold loss of affinity achieved by a Trp/Leu substitution in iCAL36, a $P^{-5}$ Trp/Ala substitution in the β-catenin C-terminus caused only a 100-fold loss of TIP-1 affinity (Zhang, et al. (2008) supra). The greater sensitivity of the iCAL36 sequence could be due to the orientation of its Trp side chain within the TIP-1 binding pocket, which differs from that observed in the TIP-1:β-catenin complex (Zhang, et al. (2008) supra). Alternatively, the differential free-energy change could be due to the different replacement side-chains (Ala vs. Leu). In particular, analysis of the TIP-1 $P^{-5}$ pocket suggests that it could not readily accommodate the larger branched Leu side chain at this position. To determine the relative contributions of Trp affinity and/or Leu incompatibility to the iCAL42 binding energy, a $P^{-5}$ alanine mutant of iCAL36 was synthesized and its binding was tested by FP displacement. The ANSRAPTSII sequence (SEQ ID NO:22) exhibited a similar lack of affinity for TIP-1 as did iCAL42. Thus, it appeared that the thermodynamic impact of the $P^{-5}$ substitution on the TIP-1:iCAL36 interaction primarily reflected the loss of the Trp side chain in stabilizing this complex, rather than a specific incompatibility of Leu.

iCAL42 is a Single-PDZ Inhibitor of Endogenous CAL.

Exploiting the localized vulnerability of the TIP-1 binding site for iCAL36, a dramatic increase in inhibitor selectivity against known off-target interactions was generated, as measured by the difference between the free energy of a given peptide binding to the CAL PDZ domain and the free energy of the same peptide binding to the highest affinity alternative among the NHERF and TIP-1 PDZ domains (ΔΔG). The SSR5 starting sequence bound CAL almost exactly as tightly as the closest NHERF1 or NHERF2 domain, N2P2 (ΔΔG-CAL-best=+0.1 kcal/mol). While the binding free energy of iCAL36 for CAL was much more favorable than for the NHERF PDZ domains (ΔΔG=−3.3 kcal/mol), it was actually 1.0 kcal/mole less favorable than for TIP-1 (ΔΔG=+1.0 kcal/mol). iCAL42 reversed this trend, binding CAL with a free energy that was substantially more favorable than any of the other partners (ΔΔG=−2.5 kcal/mol). Thus, the reward for a five-fold reduction in CAL binding affinity was a 60-fold difference relative to the $K_i$ of the PDZ domain with the next highest affinity.

To validate these observations for full-length proteins in the presence of potential physiological accessory proteins, a WCL pull-down assay was used, together with a biotinylated analog of iCAL42, BT-iCAL42. The FP competition assay was used to ensure that the selectivity profile was not compromised by the addition the N-terminal biotin linker. As expected, BT-iCAL42 bound CAL robustly ($K_i$=9.2 µM), but exhibited no appreciable binding for the NHERF and TIP-1 PDZ domains. In a WCL pull-down immunoassay, BT-iCAL42 was used as bait, and captured prey proteins were eluted by displacement with unlabeled iCAL42. When probed by western blot analysis, full-length CAL was clearly identified, but neither NHERF1, NHERF2, NHERF3, nor TIP-1 were observed.

To assess the possibility that the Trp→Leu substitution might have generated unanticipated off-target interactions, in analogy to that originally seen for iCAL36 with TIP-1, the BT-iCAL42 pull-down assay was repeated and putative interactors were resolved by TCA precipitation, SDS-PAGE, and silver staining. Aside from a modest enrichment of CAL, no protein bands were enriched in the iCAL42 eluate compared to the scrambled-peptide control eluate; nevertheless, all major bands were submitted for mass-spectrometric analysis. Consistent with western blot analysis, endogenous CAL was again clearly identified. Moreover, when the stringency of the pull-down assay was reduced, there were no other PDZ-domain containing protein in the eluate. Based on these data, among the PDZ proteins expressed in CFBE-ΔF epithelial cells, CAL was the only one with appreciable affinity for iCAL42.

F*-iCAL42 Enhances CFTR-Mediated Cl⁻ Secretion.

The strict selectivity of iCAL42 was further used to test whether the off-target TIP-1 interaction might contribute to the ΔF508-CFTR rescue seen with iCAL36. For these studies, the enhanced CAL selectivity of decapeptides carrying an N-terminal fluorescein moiety was exploited. For TIP-1, the affinity of F*-iCAL36 was only three-fold stronger than that of unlabeled iCAL36, compared to a 13-fold increase for CAL. Therefore, an N-terminally fluoresceinated version of iCAL42 (F*-iCAL42) was synthesized and binding against both CAL and TIP-1 was analyzed. In the context of the iCAL42 sequence, the addition of the N-terminal fluorescein moiety produced a five-fold enhancement in CAL affinity. Conversely, the fluoresceinated peptide showed no appreciable binding to TIP-1: at the highest protein concentration tested (150 µM), F*-iCAL42 was essentially indistinguishable from a fluoresceinated scrambled control peptide F*-SCR.

Having validated the affinity profile of the fluoresceinated probe, it was determined whether F*-iCAL42 would be able to rescue ΔF508-CFTR chloride-channel activity as efficiently as F*-iCAL36. In Ussing chamber measurements, F*-iCAL36 and F*-iCAL42 were tested in head-to-head measurements for efficacy versus the scrambled control peptide, F*-SCR. The results of this analysis indicated that F*-iCAL36 increased the $CFTR_{inh}$-172-sensitive short-circuit current ($\Delta I_{sc}$) by 10.7% (p=0.0016; n=10). Treatment of CFBE-ΔF cells with F*-iCAL42 yielded a 12.5% increase (p=0.0013; n=10) in $\Delta I_{sc}$. Thus, F*-iCAL42 was at least as efficacious as F*-iCAL36, suggesting that TIP-1 inhibition was not a substantial component of iCAL-mediated chloride-channel rescue.

Example 5

A Computationally Designed PDZ Domain Peptide Inhibitor Rescues CFTR Activity

Retrospective Validation of the K* Algorithm.

K* predictions were made for peptide sequences from a CAL peptide-array. The peptide-array binding data were used to validate the peptide inhibitor predictions. The resulting receiver operating curve (ROC) when comparing the K* scores to the CAL binding of the peptide array had an area under the curve (AUC) of 0.84, which showed that K* greatly enriched for peptides that bind CAL.

Considering if a prospective test were being conducted and the top 30 K*-ranked sequences were being tested, according to the peptide array, 11 of the top 30 sequences would be found to bind CAL. Notably, this was a 20-fold increase over the number of binders that would be expected to be found if the binding sequences were distributed randomly in the rankings.

Based on previous studies (Reynolds, et al. (2008) *J. Mol. Biol.* 382:1265-1275), CAL was known to bind the canonical sequence motif: X-S/T-X-L/V/I (SEQ ID NO:39). Therefore, a much more stringent test of the K* design algorithm was to determine the degree to which K* enriched for binders if the peptide array was restrict to sequences that matched the known CAL sequence motif. With this new restriction, K* was still able to significantly enrich for CAL peptide binders producing a ROC with an AUC of 0.71. When considering the top 30 K* ranked sequences, 17 of the 30 sequences were binders, which resulted in a 2-fold increase over the expected random distribution.

Prospective Design of CAL Peptide Inhibitors.

Since K* was able to successfully enrich for CAL binders based on peptide array data, K* was then used to prospectively find novel CAL peptide inhibitors. The K* algorithm was used to search over 2166 possible peptide hexamer inhibitors that had an N-terminal W-Q pair followed by four residues that matched the CAL PDZ sequence motif. The top-ranked sequences were chosen to be experimentally validated. The $K_i$ value for each peptide hexamer was determined using fluorescence polarization.

All of the top-ranked inhibitors were novel and none had been predicted or experimentally tested before. Unexpectedly, all of the top predicted peptides bound CAL with high affinity ($\Delta G_{binding}$ in the range of −8 to −6 kcal/mol). The best binding predicted peptide (kCAL01, WQVTRV; SEQ ID NO:23) had a $K_i$ of 2.1 µM. For comparison, the $K_i$ for the wild-type CFTR sequence (TEEEVQDTRL; SEQ ID NO:40) is 690 µM and the highest known affinity natural ligand (ANGLMQTSKL; SEQ ID NO:38) for CAL is 37 µM. Using the K* design algorithm, a peptide inhibitor with 331-fold higher affinity was obtained. Thus, the design algorithm successfully identified high affinity peptide inhibitors of the CAL PDZ domain.

The highest-affinity CAL-binding peptide hexamer (iCAL35, WQTSII; SEQ ID NO:36) identified through SPOT arrays had a $K_i$ of 14.8 µM. Seven of the eleven top tested sequences showed an improvement in binding compared to iCAL35, and kCAL01 showed a 7-fold improvement over iCAL35. The best inhibitor found through the SPOT array screens involved a fluorescein group modification to a peptide decamer (F*-iCAL36, F*-ANRSWPTSII (SEQ ID NO:19), $K_d$=1.3 μM). kCAL01 rivaled this binding affinity despite the computational search library restriction to only allow amino acids and hexamer sequences. Critically, at nearly half the size (830 Da) of F*-iCAL36, kCAL01 had approximately twice the binding efficiency (ratio of inhibitor potency to size) of F*-iCAL36 and was much closer in size to typical drugs.

Furthermore, the tight binding of the top-ranked sequences was not merely a consequence of the underlying CAL-binding motif used to select candidate sequences for evaluation. To confirm this, a set of poorly-ranked sequences was synthesized and their CAL-binding affinity was experimentally evaluated. Almost all of the poorly-ranked sequences bound CAL, consistent with their motifs. Reflecting the enrichment of CAL binders in the pool, the two poorly ranked peptides with the highest affinities ($K_i$=20 μM and 27 μM, respectively) were indeed close to the affinity of the weakest top-ranked sequence ($K_i$=18 μM). However, all of the poorly ranked peptides bound CAL more weakly than any of the top-ranked sequences, and none of them had improved affinity relative to prior biochemical efforts. Thus, K* was a powerful filter, efficiently selecting tight binders from a pool of sequences with baseline affinity for the target.

Biological Activity of the Best Designed Peptide Inhibitor.

All of the top-predicted inhibitors successfully bound CAL. This implied that the inhibitors could disrupt the degradation pathway of CFTR. However, to restore CFTR function in epithelial cells, the inhibitor must be specific for CAL and not bind other CFTR trafficking proteins. Interestingly, the top-binding predicted peptide contained a β-branched C-terminal residue (Val) that was preferred by CAL, but not by NHERF PDZ domains.

The ability of the top designed peptide, kCAL01, to restore ΔF508-CFTR function was determined by measuring ΔF508-CFTR-mediated chloride efflux in cystic fibrosis patient-derived bronchial cells expressing ΔF508-CFTR (CFBE-ΔF) using an Ussing chamber. This analysis compared ΔF508-CFTR chloride flux for a control peptide (kCAL31; WQDSGI (SEQ ID NO:41); no CAL binding expected), iCAL35, and kCAL01. While there was only a slight improvement in chloride flux for iCAL35 over the control peptide (4%), the designed peptide kCAL01 exhibited a much larger increase (12%). The 12% increase in ΔF508-CFTR chloride efflux was similar to the rescue of activity when using the selective peptide F*-iCAL36. Thus, the designed peptide kCAL01 was biologically active and of use in inhibiting the interaction between CAL and CFTR.

Example 6 iCAL Peptide Boosts Functional Rescue in Combination with a Corrector

To assess the potential for complementary action between a CAL inhibitor and a corrector, the inhibitor of CAL peptide iCAL36 (SEQ ID NO:20) was analyzed in combination with corr-4a. CF patient airway epithelial cells expressing ΔF508-CFTR (CFBE-ΔF cells) were treated with either corr-4A or DMSO and either F*-iCAL36 (fluoresceinated peptide) or a scrambled control peptide (F*-SCR). Following treatment with corr-4a alone, CFBE-ΔF monolayers showed levels of chloride-channel activity ~15% higher than the control. However, when treated with corr-4a and iCAL36, CFBE-ΔF monolayers showed ~25% increase (Cushing, et al. (2010) *Angewandte* 49:9910). Furthermore, CAL knockdown can enhance apical levels of even wild-type CFTR by >2-fold, indicating that even corrected channels can be stabilized by CAL inhibitors.

Example 7

Bioavailable CAL Inhibitor and Combination Therapy

The inhibitor of CAL peptide iCAL36 (SEQ ID NO:20) blocks the CAL PDZ binding site, extends CFTR apical half-life, and increases ΔF508-CFTR chloride currents alone and in concert with a CFTR corrector. To evaluate the therapeutic potential of a bioavailable CAL inhibitor and to test a key peptide modification strategy, the iCAL36 N-terminus was functionalized with the cell-penetrating peptide MPG (GALFLGFLGAAGSTMGAWSQPKKKRKV; SEQ ID NO:42; Morris, et al. (1997) *Nucleic Acids Res* 25:2730-2736), yielding miCAL36. Using this bioavailable CAL inhibitor in combination with a CFTR corrector such as Lumacaftor and a CFTR potentiator such as Ivacaftor, it is contemplated that all three defects (folding, gating and stability) of ΔF508-CFTR can be addressed.

What is claimed is:

1. A method for treating cystic fibrosis comprising administering to a subject in need of treatment an effective amount of an agent that selectively inhibits the interaction between a degradation-prone Cystic Fibrosis Transmembrane Conductance Regulator (CFTR) and CFTR-Associated Ligand in combination with a CFTR corrector, CFTR potentiator, mucolytic, anti-inflammatory agent or a combination thereof, thereby treating the subject's cystic fibrosis, wherein the agent is a peptide comprising the amino acid sequence of SEQ ID NO:1, or a derivative or peptidomimetic thereof.

2. The method of claim 1, wherein the degradation-prone CFTR is ΔF508 CFTR or R1066C CFTR.

3. The method of claim 1, wherein the agent is a peptide of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 or SEQ ID NO:23.

4. The method of claim 1, wherein the agent is derivatized with a label, one or more post-translational modifications, a cell-penetrating sequence, or a combination thereof.

5. The method of claim 4, wherein the cell-penetrating sequence comprises an amino acid sequence of SEQ ID NO:42.

6. The method of claim 1, wherein the peptidomimetic is a peptide of SEQ ID NO:25, SEQ ID NO:26, SEQ ID NO:27, SEQ ID NO:28, SEQ ID NO:29, SEQ ID NO:30, SEQ ID NO:31, SEQ ID NO:32 or SEQ ID NO:33.

7. A kit comprising
   (a) an agent that inhibits the interaction between a degradation-prone Cystic Fibrosis Transmembrane Conductance Regulator (CFTR) and CFTR-Associated Ligand (CAL), wherein the agent is a peptide comprising the amino acid sequence of SEQ ID NO:1, or a derivative or peptidomimetic thereof; and
   (b) a CFTR corrector, CFTR potentiator, mucolytic, anti-inflammatory agent or a combination thereof.

8. The kit of claim 7, wherein the agent is a peptide of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 or SEQ ID NO:23.

9. The kit of claim 8, wherein the agent is derivatized with a label, one or more post-translational modifications, a cell-penetrating sequence, or a combination thereof.

10. The kit of claim 9, wherein the cell-penetrating sequence comprises the amino acid sequence of SEQ ID NO:42.

11. The kit of claim 7, wherein the peptidomimetic is a peptide of SEQ ID NO:25, SEQ ID NO:26, SEQ ID NO:27, SEQ ID NO:28, SEQ ID NO:29, SEQ ID NO:30, SEQ ID NO:31, SEQ ID NO:32 or SEQ ID NO:33.

* * * * *